US008354231B2

(12) United States Patent
Kwong et al.

(10) Patent No.: US 8,354,231 B2
(45) Date of Patent: Jan. 15, 2013

(54) METHODS AND SYSTEMS FOR DETECTING AND/OR SORTING TARGETS

(75) Inventors: Gabriel A. Kwong, Alhambra, CA (US); Ryan C. Bailey, Urbana, IL (US); Rong Fan, Pasadena, CA (US); James R. Heath, South Pasadena, CA (US)

(73) Assignee: Cal. Inst. Tech., Pasadena, CA (US)

( * ) Notice: Subject to any disclaimer, the term of this patent is extended or adjusted under 35 U.S.C. 154(b) by 234 days.

(21) Appl. No.: 12/652,000

(22) Filed: Jan. 4, 2010

(65) Prior Publication Data

US 2011/0039717 A1 Feb. 17, 2011

Related U.S. Application Data

(63) Continuation of application No. 11/888,502, filed on Aug. 1, 2007, now abandoned.

(60) Provisional application No. 60/834,823, filed on Aug. 2, 2006, provisional application No. 60/959,665, filed on Jul. 16, 2007.

(51) Int. Cl.
*C12Q 1/68* (2006.01)
*G01N 33/53* (2006.01)

(52) U.S. Cl. ............. 435/6.12; 435/7.1; 435/287.2; 435/288.3

(58) Field of Classification Search ............ 435/6.12, 435/7.1, 287.2, 288.3
See application file for complete search history.

(56) References Cited

U.S. PATENT DOCUMENTS

| | | | |
|---|---|---|---|
| 5,700,637 A * | 12/1997 | Southern | 435/6.12 |
| 6,518,018 B1 * | 2/2003 | Szostak et al. | 435/6.1 |
| 6,924,153 B1 | 8/2005 | Boehringer et al. | 436/514 |
| 7,491,516 B2 * | 2/2009 | Collinson et al. | 435/70.21 |
| 2002/0146745 A1 | 10/2002 | Natan et al. | |
| 2002/0168640 A1 * | 11/2002 | Li et al. | 435/6 |
| 2003/0013091 A1 | 1/2003 | Dimitrov | |
| 2003/0082601 A1 | 5/2003 | Dill | 435/6 |
| 2009/0036324 A1 | 2/2009 | Fan et al. | 506/9 |

FOREIGN PATENT DOCUMENTS

| | | |
|---|---|---|
| CN | 1254845 A | 5/2000 |
| CN | 1749752 A | 3/2006 |
| EP | 1672082 A2 | 6/2006 |
| EP | 1816476 | 8/2007 |
| WO | 99/11777 | 3/1999 |
| WO | 02/064825 A2 | 8/2002 |
| WO | 2007/014267 | 2/2007 |
| WO | 2008/016680 | 2/2008 |

OTHER PUBLICATIONS

International Search Report for PCT/US2009/040106 filed on Apr. 9, 2009 in the name of California Institute of Technology et al.
Written Opinion for PCT/US2009/040106 filed on Apr. 9, 2009 in the name of California Institute of Technology et al.
Written Opinion for PCT/US2007/017258 filed on Aug. 1, 2007 in the name of California Institute of Technology et al.
Restriction Requirement issued by USPTO for U.S. Appl. No. 12/174,601 dated Aug. 4, 2009.
Restriction Requirement issued by USPTO for U.S. Appl. No. 12/174,601 dated Jan. 6, 2010.
Office Action issued by USPTO for U.S. Appl. No. 12/174,598 dated Jun. 29, 2009.
Restriction Requirement issued by USPTO for U.S. Appl. No. 11/888,502 dated Jan. 30, 2009.
Office Action issued by USPTO for U.S. Appl. No. 11/888,502 dated Jul. 8, 2009.
Adler, M, et al. Detection of femtogram amounts of biogenic amines using self-assembled DNA-protein nanostructures. Nature Methods, vol. 2, No. 2, pp. 147-149, Feb. 2005.
Becker, C.F.W., et al. Direct Readout of Protein-Protein Interactions by Mass Spectrometry from Protein-DNA Microarrays. Angew. Chem. Int. Ed., 44, pp. 7635-7639, 2005.
Chen, D.S., et al. Marked Differences in Human Melanoma Antigen-Specific T Cell Responsiveness after Vaccination Using a Functional Microarray. PLoS Medicine, vol. 2, Issue 10, pp. 1018-1030, Oct. 2005.
Engvall, E. et al. Enzyme-linked immunosorbent assay, ELISA .3. quantitation of specific antibodies by enzyme-labeled anti-immunoglobulin in antigen-coated tubes. J. Immunol. vol. 109, pp. 129-135, 1972.
Hong, J.W., et al. A nanoliter-scale nucleic acid processor with parallel architecture. Nature Biotechnology, vol. 22, No. 4, pp. 435-439, Apr. 2004.
Park, S.J., et al. Array-Based Electrical Detection of DNA with Nanoparticle Probes. Science, vol. 295, pp. 1503-1506, Feb. 22, 2002.
Sano, T. et al. Immuno-PCR: very sensitive antigen detection by means of specific antibody-DNA conjugates. Science, vol. 258, pp. 120-122, 1992.
Wacker, R. and Niemeyer, C.M. DDI- μFIA—A Readily Configurable Microarray-Fluorescence Immunoassay Based on DNA-Directed Immobilization of Proteins. ChemBioChem, 5, pp. 453-459, 2004.
Bailey, R.C., et al, "DNA-Encoded Antibody Libraries: A Unified Platform for Multiplexed Cell Sorting and Detection of Genes and Proteins", J. Am. Chem. Soc. 129:1959-1987 (2007).
Dirks, R.M., et al. "Paradigms for computational nucleic acid design", Nucleic Acid Res. 32(4):1392-1403 (2004).
Halpin, D.R., et al , "DNA Display II Genetic Manipulation of Combinational Chemistry Libraries for Small-Molecule Evolution", PLos Biol. 2(7):1022-1030 (2004).
Scheuermann, J., et al "DNA-encoded chemical libraries", J. Biotechnol. 126:568-581 (2006).
Stoeva, S.I., et al., "Multiplexed Detection of Protein Cancer Markers with Biobarcoded Nanoparticle Probes", J. Am. Chem. Soc. 128:8378-8379 (2006).

* cited by examiner

*Primary Examiner* — Kenneth R. Horlick
*Assistant Examiner* — Joyce Tung
(74) *Attorney, Agent, or Firm* — Sean M. Coughlin, Esq.; Lathrop & Gage LLP

(57) ABSTRACT

Provided herein are methods and systems for detecting and/or sorting targets in a sample based on the combined use of polynucleotide-encoded protein and substrate polynucleotides. The polynucleotide-encoded protein is comprised of a protein that specifically binds to a predetermined target and of an encoding polynucleotide that specifically binds to a substrate polynucleotide, wherein the substrate polynucleotide is attached to a substrate.

6 Claims, 23 Drawing Sheets a. b.

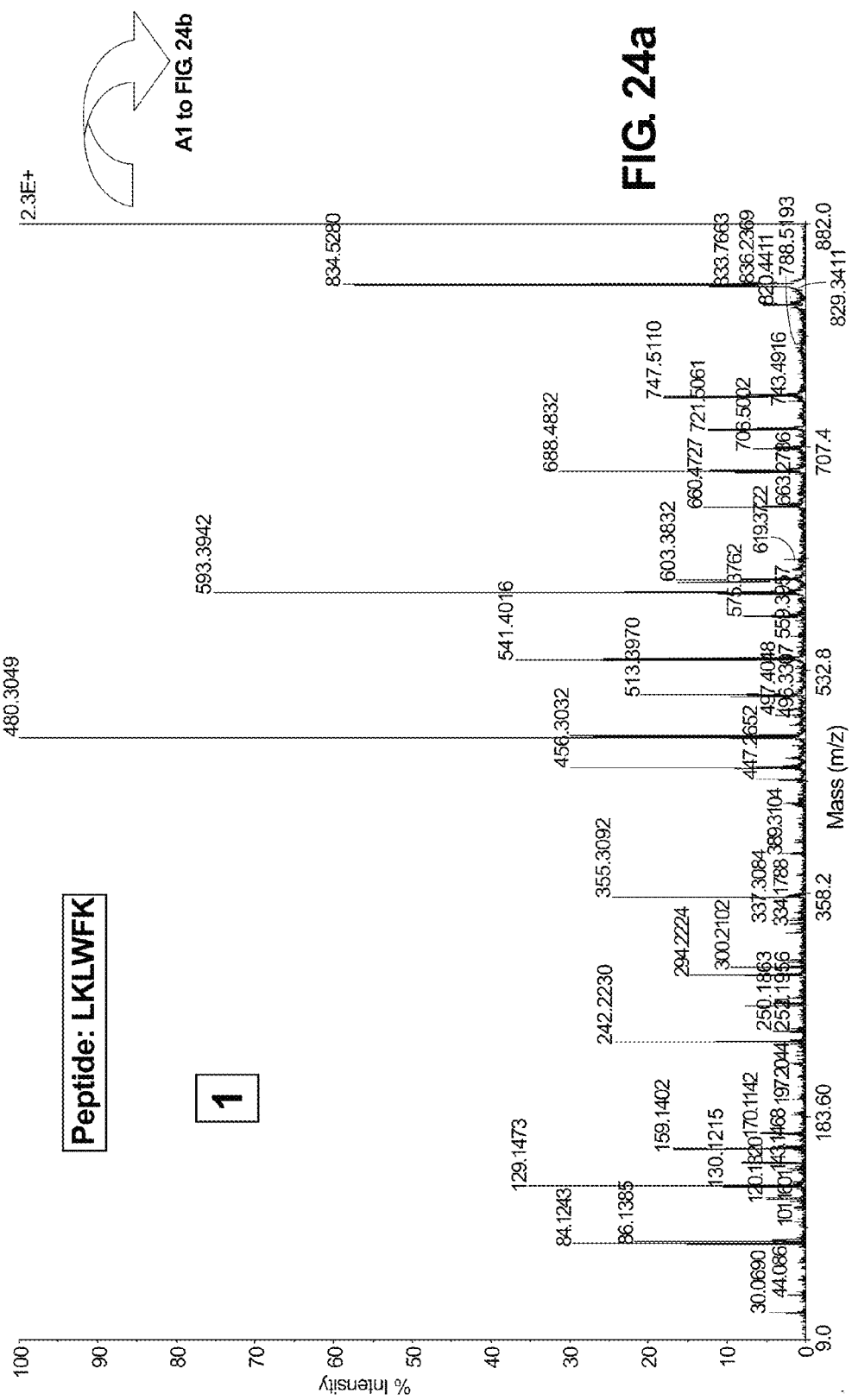

A1 from FIG. 24a
FIG. 24b
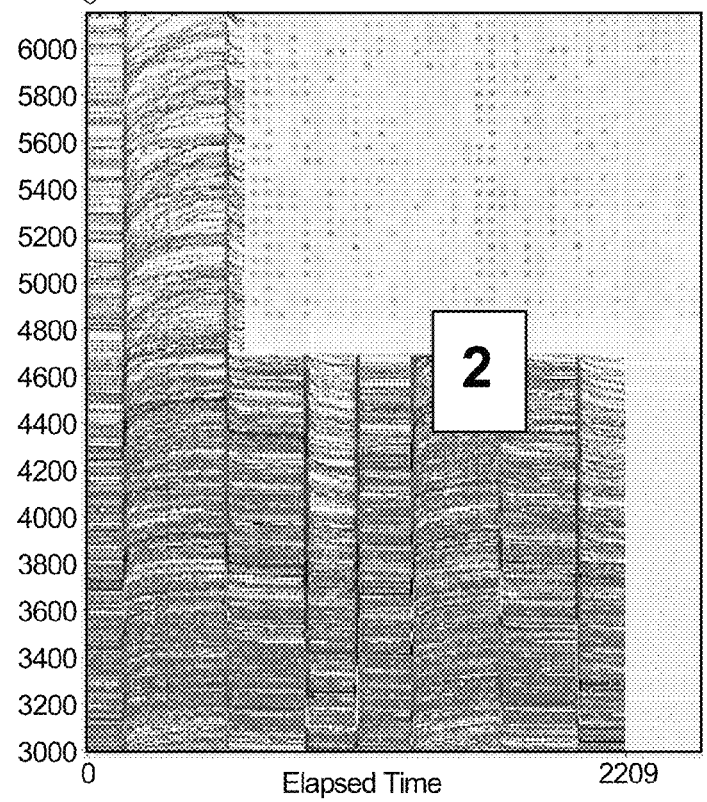
Elapsed Time
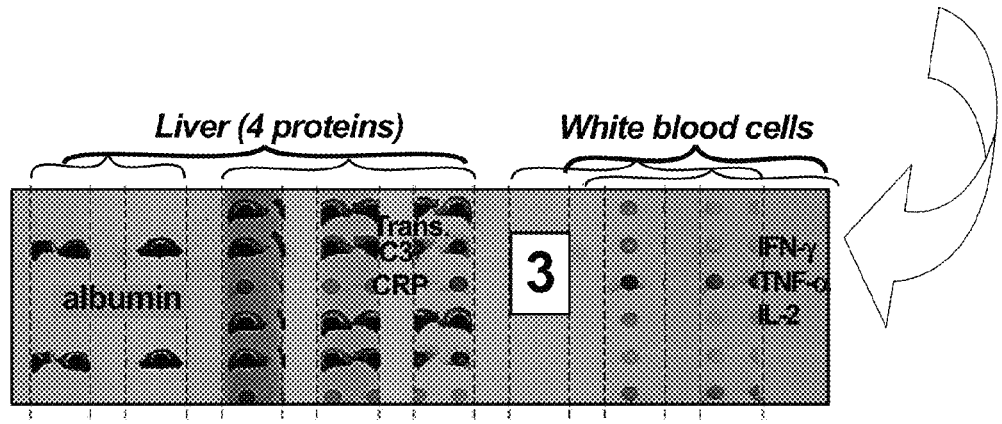
FIG. 24c

SEQUENCE LISTING

<160> NUMBER OF SEQ ID NOS: 18

<210> SEQ ID NO 1
<211> LENGTH: 26
<212> TYPE: DNA
<213> ORGANISM: artificial sequence
<220> FEATURE:
<223> OTHER INFORMATION: Synthetic oligonucleotide

<400> SEQUENCE: 1
aaaaaaaaaa cgtgacatca tgcatg                                              26

<210> SEQ ID NO 2
<211> LENGTH: 26
<212> TYPE: DNA
<213> ORGANISM: artificial sequence
<220> FEATURE:
<223> OTHER INFORMATION: Synthetic oligonucleotide

<400> SEQUENCE: 2
aaaaaaaaaa catgcatgat gtcacg                                              26

<210> SEQ ID NO 3
<211> LENGTH: 26
<212> TYPE: DNA
<213> ORGANISM: artificial sequence
<220> FEATURE:
<223> OTHER INFORMATION: Synthetic oligonucleotide

<400> SEQUENCE: 3
aaaaaaaaaa ggattcgcat accagt                                              26

<210> SEQ ID NO 4
<211> LENGTH: 26
<212> TYPE: DNA
<213> ORGANISM: artificial sequence
<220> FEATURE:
<223> OTHER INFORMATION: Synthetic oligonucleotide

<400> SEQUENCE: 4
aaaaaaaaaa actggtatgc gaatcc                                              26

<210> SEQ ID NO 5
<211> LENGTH: 26
<212> TYPE: DNA
<213> ORGANISM: artificial sequence
<220> FEATURE:
<223> OTHER INFORMATION: Synthetic oligonucleotide

<400> SEQUENCE: 5
aaaaaaaaaa tggacgcatt gcacat                                              26

<210> SEQ ID NO 6
<211> LENGTH: 26
<212> TYPE: DNA
<213> ORGANISM: artificial sequence
<220> FEATURE:
<223> OTHER INFORMATION: Synthetic oligonucleotide

<400> SEQUENCE: 6
aaaaaaaaaa atgtgcaatg cgtcca                                              26

<210> SEQ ID NO 7
<211> LENGTH: 30
<212> TYPE: DNA

```
<213> ORGANISM: artificial sequence
<220> FEATURE:
<223> OTHER INFORMATION: Synthetic oligonucleotide

<400> SEQUENCE: 7
aaaaaaaaaa atcctggagc taagtccgta                                          30

<210> SEQ ID NO 8
<211> LENGTH: 30
<212> TYPE: DNA
<213> ORGANISM: artificial sequence
<220> FEATURE:
<223> OTHER INFORMATION: Synthetic oligonucleotide

<400> SEQUENCE: 8
aaaaaaaaaa tacggactta gctccaggat                                          30

<210> SEQ ID NO 9
<211> LENGTH: 30
<212> TYPE: DNA
<213> ORGANISM: artificial sequence
<220> FEATURE:
<223> OTHER INFORMATION: Synthetic oligonucleotide

<400> SEQUENCE: 9
aaaaaaaaaa gcctcattga atcatgccta                                          30

<210> SEQ ID NO 10
<211> LENGTH: 30
<212> TYPE: DNA
<213> ORGANISM: artificial sequence
<220> FEATURE:
<223> OTHER INFORMATION: Synthetic oligonucleotide

<400> SEQUENCE: 10
aaaaaaaaaa taggcatgat tcaatgaggc                                          30

<210> SEQ ID NO 11
<211> LENGTH: 31
<212> TYPE: DNA
<213> ORGANISM: artificial sequence
<220> FEATURE:
<223> OTHER INFORMATION: Synthetic oligonucleotide

<400> SEQUENCE: 11
aaaaaaaaaa agcactcgtc tactatcgct a                                        31

<210> SEQ ID NO 12
<211> LENGTH: 30
<212> TYPE: DNA
<213> ORGANISM: artificial sequence
<220> FEATURE:
<223> OTHER INFORMATION: Synthetic oligonucleotide

<400> SEQUENCE: 12
aaaaaaaaaa tagcgatagt agacgagtgc                                          30

<210> SEQ ID NO 13
<211> LENGTH: 30
<212> TYPE: DNA
<213> ORGANISM: artificial sequence
<220> FEATURE:
<223> OTHER INFORMATION: Synthetic oligonucleotide

<400> SEQUENCE: 13
aaaaaaaaaa atggtcgaga tgtcagagta                                          30
```

```
<210> SEQ ID NO 14
<211> LENGTH: 30
<212> TYPE: DNA
<213> ORGANISM: artificial sequence
<220> FEATURE:
<223> OTHER INFORMATION: Synthetic oligonucleotide

<400> SEQUENCE: 14
aaaaaaaaaa tactctgaca tctcgaccat                                30

<210> SEQ ID NO 15
<211> LENGTH: 30
<212> TYPE: DNA
<213> ORGANISM: artificial sequence
<220> FEATURE:
<223> OTHER INFORMATION: Synthetic oligonucleotide

<400> SEQUENCE: 15
aaaaaaaaaa atgtgaagtg gcagtatcta                                30

<210> SEQ ID NO 16
<211> LENGTH: 30
<212> TYPE: DNA
<213> ORGANISM: artificial sequence
<220> FEATURE:
<223> OTHER INFORMATION: Synthetic oligonucleotide

<400> SEQUENCE: 16
aaaaaaaaaa tagatactgc cacttcacat                                30

<210> SEQ ID NO 17
<211> LENGTH: 30
<212> TYPE: DNA
<213> ORGANISM: artificial sequence
<220> FEATURE:
<223> OTHER INFORMATION: Synthetic oligonucleotide

<400> SEQUENCE: 17
aaaaaaaaaa atcaggtaag gttcacggta                                30

<210> SEQ ID NO 18
<211> LENGTH: 31
<212> TYPE: DNA
<213> ORGANISM: artificial sequence
<220> FEATURE:
<223> OTHER INFORMATION: Synthetic oligonucleotide

<400> SEQUENCE: 18
aaaaaaaaaa ttaccgtgaa ccttacctga t                              31
```

METHODS AND SYSTEMS FOR DETECTING AND/OR SORTING TARGETS

CROSS REFERENCE TO RELATED APPLICATIONS

This application is the continuation of U.S. patent application Ser. No. 11/888,502 filed on Aug. 1, 2007, which is incorporated herein by reference in its entirety, and which, in turn, claims priority to U.S. Provisional Application entitled "A unified Platform for Multiplexed Cell Sorting and Detection of Genes and Proteins" Ser. No. 60/834,823, filed on Aug. 2, 2006, and to U.S. Provisional Application entitled "Digital DEAL: A quantitative and digital Protein Detection Immunoassay" Ser. No. 60/959,665 filed on Jul. 16, 2007, the disclosures of which are incorporated herein by reference in their entirety.

STATEMENT OF GOVERNMENT GRANT

The U.S. Government has certain rights in this disclosure pursuant to Grant No. CA119347 awarded by the National Cancer Institute at Frederick and pursuant to Grant No. DAAD19-03-D-0004/0008 and Grant No. 5U54CA119347 awarded by ARO-US Army Robert Morris Acquisition Center.

TECHNICAL FIELD

The present disclosure relates to detection of one or more targets, in particular biomarkers, in a sample such as a biological sample. More specifically, it relates to methods and systems for detecting and/or sorting targets.

BACKGROUND

High sensitivity detection of targets and in particular of biomarkers has been a challenge in the field of biological molecule analysis, in particular when aimed at detection of a plurality of targets. Whether for pathological examination or for fundamental biology studies, several methods are commonly used for the detection of various classes of biomaterials and biomolecules.

Some of the techniques most commonly used in the laboratory for detection of single biological targets include gel electrophoresis, polyacrylamide gel electrophoresis (PAGE), western blots, fluorescent in situ hybridization (FISH), Florescent activated cell sorting (FACS), Polymerase chain reaction (PCR), and enzyme linked immunosorbent assay (ELISA). These methods have provided the ability to detect one or more biomarkers in biological samples such as tissues and are also suitable for diagnostic purposes.

However, current global genomic and proteomic analyses of tissues are impacting our molecular-level understanding of many human cancers. Particularly informative are studies that integrate both gene expression and proteomic data. Such multiparameter data sets are beginning to reveal the perturbed regulatory networks which define the onset and progression of cancers (Lin, B.; White, J. T.; Lu, W.; Xie, T.; Utleg, A. G.; Yan, X.; Yi, E. C.; Shannon, P.; Khretbukova, I.; Lange, P. H.; Goodlett, D. R.; Zhou, D.; Vasicek, T. J.; Hood, L. *Cancer Res.* 2005, 65, 3081-3091. Kwong, K. Y.; Bloom, G. C.; Yang, I.; Boulware, D.; Coppola, D.; Haseman, J.; Chen, E.; McGrath, A.; Makusky, A. J.; Taylor, J.; Steiner, S.; Zhou, J.; Yeatman, T. J.; Quackenbush, J. *Genomics* 2005, 86, 142-158. Huber, M.; Bahr, I.; Kratzchmar, J. R.; Becker, A.; Muller, E.-C.; Donner, P.; Pohlenz, H.-D.; Schneider, M. R.; Sommer, A. *Molec. Cell. Proteomics* 2004, 3, 43-55. Tian, Q.; Stepaniants, S. B.; Mao, M.; Weng, L.; Feetham, M. C.; Doyle, M. J.; Yi, E. C.; Dai, H.; Thorsson, V.; Eng, J.; Goodlett, D.; Berger, J. P.; Gunter, B.; Linseley, P. S.; Stoughton, R. B.; Aebersold, R.; Collins, S. J.; Hanlon, W. A.; Hood, L. E. *Molec. Cell. Proteomics* 2004, 3, 960-969. Chen, G.; Gharib, T. G.; Huang, C.-C.; Taylor, J. M. G.; Misek, D. E.; Kardia, S. L. R.; Giordano, T. J.; Iannettoni, M. D.; Orringer, M. B.; Hanash, S. M.; Beer, D. G. *Molec. Cell. Proteomics* 2002, 1, 304-313). This new picture of complex diseases such as cancer, and the emergence of promising new cancer drugs (Prados, M.; Chang, S.; Burton, E.; Kapadia, A.; Rabbitt, J.; Page, M.; Federoff, A.; Kelly, S.; Fyfe, G. *Proc. Am. Soc. Clin. Oncology* 2003, 22, 99. Rich, J. N.; Reardon, D. A.; Peery, T.; Dowell, J. M.; Quinn, J. A.; Penne, K. L.; Wikstrand, C. J.; van Duyn, L. B.; Dancey, J. E.; McLendon, R. E.; Kao, J. C.; Stenzel, T. T.; Rasheed, B. K. A.; Tourt-Uhlig, S. E.; Herndon, J. E.; Vredenburgh, J. J.; Sampson, J. H.; Friedman, A. H.; Bigner, D. D.; Friedman, H. S. *J. Clin. Oncology* 2004, 22, 133-142.), are placing new demands on clinical pathology (Mellinghoff, I. K.; Wang, M. Y.; Vivanco, I.; Haas-Kogan, D. A.; Zhu, S.; Dia, E. Q.; Lu, K. V.; Yoshimoto, K.; Huang, J. H. Y.; Chute, D. J.; Riggs, B. L.; Horvath, S.; Liau., L. M.; Cavenee, W. K.; Rao, P. N.; Beroukhim, R.; Peck, T. C.; Lee, J. C.; Sellers, W. R.; Stokoe, D.; Prados, M.; Cloughesy, T. F.; Sawyers, C. L.; Mischel, P. S. *N. Engl. J. Med.* 2006, 353, 2012-2024). For example, traditional pathology practices (i.e. microscopic analysis of tissues) does not distinguish potential responders from non-responders for the new cancer molecular therapeutics (Betensky, R. A.; Louis, D. N.; Cairncross, J. G. *J. Clin. Oncology* 2002, 20, 2495-2499). Recent examples exist in which pauciparameter molecular measurements are being employed to identify potential responders to at least two therapauetics (Hughes, T.; Branford, S., 2003. *Semin Hematol.* 2 Suppl 2, 62-68. Lamb, J.; Crawford, E. D.; Peck, D.; Modell, J. W.; Blat, I. C.; Wrobel, M. J.; Lerner, J.; Brunet, J. P.; Subramanian, A.; Ross, K. N.; Reich, M.; Hieronymus, H.; Wei, G.; Armstrong, S. A.; Haggarty, S. J.; Clemons, P. A.; Wei, R.; Carr, S. A.; Lander, E. S.; Golub, T. R., *Science* 2006, 313, (5795), 1929-1935. Martin, M., *Clin. Transl Oncol.* 8, (1), 7-14. Radich, J. P.; Dai, H.; Mao, M.; Oehler, V.; Schelter, J.; Druker, B.; Sawyers, C. L.; Shah, N.; Stock, W.; Willman, C. L.; Friend, S.; Linsley, P. S., *Proc. Natl. Acad. Sci.* 2006, 103, (8), 2794-2799). However, it is unlikely that single-parameter measurements will be the norm. Instead, the coupling of molecular diagnostics with molecular therapeutics will eventually require measurements of a multiparameter (e.g. cells, mRNAs and proteins) biomarker panel that can be used to direct patients to appropriate therapies or combination therapies.

Currently, the measurement of a multiparameter panel of biomarkers from diseased tissues requires combinations of microscopic analysis, microarray data (Mischel, P. S.; Cloughesy, T. F.; Nelson, S. F. *Nature Rev. Neuroscience* 2004, 5, 782-794), immunohistochemical staining, Western Blots (Mellinghoff, I. K.; Wang, M. Y.; Vivanco, I.; Haas-Kogan, D. A.; Zhu, S.; Dia, E. Q.; Lu, K. V.; Yoshimoto, K.; Huang, J. H. Y.; Chute, D. J.; Riggs, B. L.; Horvath, S.; Liau., L. M.; Cavenee, W. K.; Rao, P. N.; Beroukhim, R.; Peck, T. C.; Lee, J. C.; Sellers, W. R.; Stokoe, D.; Prados, M.; Cloughesy, T. F.; Sawyers, C. L.; Mischel, P. S. *N. Engl. J. Med.* 2006, 353, 2012-2024), and other methods. The collected data is integrated together within some model for the disease, such as a cancer pathway model (Weinberg, R. A., *Cancer Biology*. Garland Science: 2006), to generate a diagnosis. Currently, performing these various measurements requires a surgically resected tissue sample. The heterogeneity of such biopsies

SUMMARY

Provided herein, are methods and systems based on the use of a polynucleotide-encoded protein in combination with a substrate polynucleotide. The polynucleotide-encoded protein herein disclosed is comprised of a protein that specifically binds to a target and of an encoding-polynucleotide attached to the protein. The encoding polynucleotide is comprised of a sequence that specifically binds to a substrate polynucleotide. The substrate polynucleotide herein disclosed is attached to a substrate and is comprised of a sequence that specifically binds to the encoding polynucleotide.

Several assays, including but not limited to assays for the detection and/or separation of targets, in particular biomarkers, such as cells, proteins and/or polynucleotides, can be performed according to the methods and systems herein disclosed. In particular, in the assays with the methods and systems herein disclosed, the polynucleotide-encoded protein is used to specifically bind to a target in a polynucleotide-encoded protein-target complex, and the substrate polynucleotide is used to bind the polynucleotide-encoded protein-target complex to the substrate for detection. The methods and systems herein disclosed allow the advantageous performance of several assays in particular, in a microfluidic environment as it will be apparent to a skilled person upon reading of the present disclosure.

According to a first aspect, a method and a system to detect a target in a sample are disclosed, the method and system based on the combined use of a substrate polynucleotide attached to a substrate, and a polynucleotide-encoded protein comprised of a protein that specifically binds to the target and of an encoding polynucleotide that specifically binds to the substrate polynucleotide attached to the substrate.

In the method, the polynucleotide-encoded protein is contacted with the sample and the substrate polynucleotide for a time and under conditions to allow binding of the polynucleotide-encoded protein with the target in a polynucleotide-encoded protein-target complex, and binding of the encoding polynucleotide with the substrate polynucleotide thus providing a polynucleotide-encoded protein-target complex bound to the substrate polynucleotide. In the method, the polynucleotide-encoded protein-target complex bound to the substrate polynucleotide is then detected by way of detecting techniques which will be identifiable by a skilled person upon reading of the present disclosure.

In the system, a substrate with a substrate polynucleotide attached to the substrate is provided, together with a polynucleotide-encoded protein comprising a protein that specifically binds to the target and an encoding-polynucleotide that specifically binds to the substrate polynucleotide.

According to a second aspect, a method and a system for detecting a plurality of targets in a sample are disclosed, the method and system based on the combined use of a plurality of substrate polynucleotides attached to a substrate and a plurality of polynucleotide-encoded antibodies.

In the method and system, each of the substrate polynucleotides is sequence specific and positionally distinguishable from another. In the method and system, each of the polynucleotide-encoded proteins is comprised of a protein that specifically binds to a predetermined target of the plurality of targets and of an encoding polynucleotide that specifically binds to a sequence specific and positionally distinguishable substrate polynucleotide of the plurality of substrate polynucleotides. Further, in the method and system, each protein and encoding polynucleotide is bindingly distinguishable from another.

In the method, the plurality of polynucleotide-encoded antibodies is contacted with the sample and the plurality of substrate polynucleotides for a time and under conditions to allow binding of the antibodies with the targets in a plurality of polynucleotide-encoded protein-target complexes and binding of the encoding polynucleotides to the substrate polynucleotides. In the method, the plurality of polynucleotide-encoded protein-target complexes bound to the plurality of substrate polynucleotides on the substrate is then detected by way of detecting techniques that will be identifiable by the skilled person upon reading of the present disclosure.

In the system, a substrate with the plurality substrate polynucleotides attached to the substrate is comprised, together with the plurality of polynucleotide-encoded antibodies.

According to a third aspect, a method and a system for detecting a plurality of targets in a sample, are disclosed, wherein the targets comprise at least one target polynucleotide. The method and system are based on the combined use of a plurality of substrate polynucleotides attached to a substrate, at least one polynucleotide-encoded protein and at least one labeled polynucleotide.

In the method and system, each substrate polynucleotide is sequence-specific and positionally distinguishable from another. In the method and system, the at least one labeled polynucleotide specifically binds to the at least one target polynucleotide, with each labeled polynucleotide bindingly distinguishable from another. In the method and system, the at least one polynucleotide-encoded protein is comprised of a protein that specifically binds to a predetermined target of the plurality of the targets and of an encoding polynucleotide that specifically binds to a sequence-specific and positionally distinguishable substrate polynucleotide of the plurality of substrate polynucleotides. In the method and system, each protein and encoding polynucleotide is bindingly distinguishable from another, each protein is further bindingly distinguishable from each labeled polynucleotide, and each polynucleotide-encoded protein is bindingly distinguishable from each labeled target polynucleotide In the method, the at least one labeled polynucleotide is contacted with the sample for a time and under conditions to allow binding of the labeled polynucleotide with the target polynucleotide to provide at least one labeled target polynucleotide, wherein the at least one labeled target polynucleotides is comprised of a sequence that specifically binds to a sequence-specific and positionally distinguishable substrate polynucleotide. Additionally, in the method, the at least one polynucleotide-encoded protein is contacted with the sample for a time and under conditions to allow binding of the protein with the target, in at least one polynucleotide-encoded protein-target complex. Further, in the method, the at least one labeled target polynucleotide and the at least one polynucleotide-encoded protein-target complex are contacted with the plurality of substrate polynucleotides for a time and under conditions to allow binding of the at least one labeled target polynucleotide with a corresponding substrate polynucleotide and binding of the at least one encoding polynucleotide with a corresponding substrate polynucleotide. In the method, the labeled target polynucleotides and the polynucleotide-encoded protein-target complexes bound to the plurality of spatially located substrate polynucleotides on the substrate are then detected by use of detecting techniques that will be identifiable by the skilled person upon reading of the present disclosure.

In the system, a substrate with the plurality of substrate polynucleotides attached to the substrate is comprised together with, the at least one labeled polynucleotide and the at least one polynucleotide-encoded-protein. In the system, the at least one labeled polynucleotide of the system is for the production of a labeled target polynucleotide that specifically binds to a sequence-specific and positionally distinguishable substrate polynucleotide.

According to a fourth aspect, a method and system for sorting targets of a plurality of targets is disclosed, the method and system based on the combined use of a plurality of substrate polynucleotides attached to a substrate and a plurality of polynucleotide-encoded antibodies. In some embodiments the targets are cells and the method and systems are for sorting a plurality of cells.

In the method and system, each substrate polynucleotide is sequence-specific and positionally distinguishable from another. In the method and system, each polynucleotide-encoded protein is comprised of a protein and of a encoding polynucleotide attached to the protein, wherein the protein specifically binds to a predetermined target of the plurality of targets and the encoding polynucleotide specifically binds to a sequence-specific and positionally distinguishable substrate polynucleotide of the plurality of substrate polynucleotides. In the method and system, each protein and encoding polynucleotide is bindingly distinguishable from another.

In the method, the plurality of polynucleotide-encoded antibodies is contacted with the sample for a time and under conditions to allow binding of the antibodies with the targets, thus providing a plurality of polynucleotide-encoded protein-target complexes. In the method the plurality of polynucleotide-encoded protein-target complexes is then contacted with the plurality of substrate polynucleotides for a time and under conditions to allow binding of the encoding polynucleotides to the substrate polynucleotides attached to the substrate, thus sorting the plurality of targets in a plurality of polynucleotide-encoded protein-target complexes bound to the substrate.

In the system, a substrate with the plurality of substrate polynucleotides attached to the substrate is comprised together with the plurality of polynucleotide-encoded antibodies.

According to a fifth aspect, an array for the detection of one or more targets in a sample fluid is disclosed, the array comprising a substrate with a plurality of substrate polynucleotides attached to said substrate component, the substrate polynucleotide sequence specific and positionally distinguishable, wherein each of the substrate polynucleotides is comprised of a sequence that is orthogonal to the sequence of another substrate polynucleotide.

According to a sixth aspect, the substrate of each of the methods, systems and arrays disclosed herein is in operable association with a microfluidic component comprising a microfluidic feature for carrying a fluid. Accordingly, in the methods, at least contacting the encoding-polynucleotide and/or the labeled polynucleotide target with the substrate polynucleotide, can be performed in the fluid carried by the microfluidic feature. Additionally, each of the systems herein disclosed can further include the microfluidic component comprising the microfluidic feature.

A first advantage of the methods and systems disclosed herein is that, in each of the methods and systems herein disclosed, contacting the polynucleotide-encoded protein to the target can be performed before the protein is bound to the substrate. As a consequence, with targets such as cells, access of the target to the binding site of the protein cannot be impaired by the substrate and both the protein and the target molecule will have a complete orientational freedom in performing the contact, thus improving the sensitivity of any related assay performed with the disclosed methods and systems.

A second advantage of the methods and systems disclosed herein is that each of the methods and systems herein disclosed the polynucleotide-encoded proteins can be assembled in solution, thereby minimizing the effect of protein denaturation associated to prior art methods, which include drying the substrate after binding and elevated temperature (e.g., close to 100° C.). In some of those prior art methods, protein arrays are generated by spotting via a fine pin onto a glass substrate, so that the manufacturer steps needs to be closely monitored to ensure that the proteins do not dry out and hence denature. On the contrary, in the methods and systems herein disclosed the proteins can be assembled onto the substrate in solution, so to minimize to zero proteins drying out and denaturation.

A third advantage of the methods and systems disclosed herein is that in each of the methods and systems herein disclosed, biofouling, i.e. non-specific binding of non-encoded protein to the substrate, is greatly reduced when compared to the protein-based methods and systems of the art, therefore allowing a more efficient binding and, when detection is desired, a more accurate quantitative detection of the target molecule in the sample when compared with antibodies based methods and system of the art.

A fourth advantage of the methods and systems disclosed herein, is that the multiplexed detection and/or separation of a higher number of targets can be performed when compared to the protein-based methods and systems of the art. This is due to several factors. A first factor is that the reduced biofouling associated with the use of a polynucleotide-encoded protein in combination with a substrate polynucleotide attached to a substrate allows a more efficient binding and detection of the polynucleotide-encoded protein-target complexes to the substrate. A second factor is that the size of the substrate polynucleotide in the method system herein disclosed is much smaller, than the corresponding anchoring molecules used in the protein-based methods and systems of the art. As a consequence, a higher density of proteins can be assembled on the substrate in comparison with the prior art techniques (e.g., about 5,000 spots per square inch versus 96 well plates of techniques like ELISA).

A fifth advantage of the methods and systems disclosed herein is that in each of the methods and systems herein disclosed it is possible to detect and separate in a single substrate chemically different targets, including biomarkers such as polynucleotides, proteins, and cells that have a different surface marker. Accordingly, the methods and systems herein disclosed allow the multiplexed detection and/or separation of genes, proteins and cells within the same environment.

A further advantage of the methods and systems for sorting targets herein disclosed, is that the methods and systems herein disclosed make the sorted cells immediately available for post-sorting analysis, which is particularly relevant in the embodiments wherein the targets are cells that are made available for post-sorting analysis of gene and protein expression in the cells.

An additional advantage of the methods and systems herein disclosed when used to perform diagnostic assays is that multiplexed detection of multiple biomarkers from a same region of tissue can be performed on a single substrate. A further advantage of the methods and systems used to perform diagnostic assays is that the biomarkers can be chemically distinct biomarkers such as cells, mRNAs and proteins and that the detection can be a quantitative detection and/or a qualitative. A still further advantage of the methods and systems herein disclosed when used to perform a diagnostic assay is that they allow detection of complex genomic and/or proteomic profiles that, when compared with pre-determined profiles provide diagnostic indications for diseases characterized by perturbed regulatory networks, such as cancer. Another advantage of the methods and systems herein disclosed when used to perform a diagnostic assay, is the possibility to analyze a small amount of biological sample in a multiparameter fashion, and be able to bridge the three relevant areas of biological information, that of the genes (represented by DNA), proteins, and cells.

Further remarkable advantages of all the methods and systems herein disclosed when the substrate is in operable association with a microfluidic component, are to allow performance of multiplexed multiparameter assays with a sample greatly reduced in size, in a reduced time and with a reduced number of steps when compared to corresponding methods and systems of the art. In particular, the multiplexed multiparameter microfluidic methods and systems herein disclosed are particularly advantageous when the targets are biomarkers from a tissue in view of the reduced amount of sample required to perform the analysis which minimizes the need to euthanize mice. Additionally, the methods and systems performed in a microfluidic environment herein disclosed, allow a detection of a target that is included in a sample in a small quantities allowing detection of molecules present in the sample at a concentration down to about a 10 femtoMolar.

Still further advantages of the methods and systems herein disclosed, when the substrate is in operable association with a microfluidic component when used to perform a diagnostic assay, are to allow the multiplexed detection of biomarkers, including chemically distinct biomarkers such as polynucleotides, proteins and cells. A further additional advantage of the diagnostic methods and systems herein disclosed, in embodiments wherein the substrate is in operable association with a microfluidic component, is to allow performance of multiplexed multiparameter assays on a single sample from the same microscopic region of an heterogeneous tissue. As a consequence, the methods and systems herein disclosed also minimize the sampling errors associated with heterogeneous biopsies required to perform the various measurements of the diagnostic method and systems for the detection of multiple chemically distinct biomarkers of the art.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description, serve to explain the principles and implementations of the disclosure.

In the drawings:

FIG. 24 illustrates the pathway from serum biomarker discovery via tandem mass spectrometry (Panel a or 1) to antibody validation and selection (Panel c or 3) via large scale SPR (Panel b or 2) to validating clinical pathways with an embodiment of the methods and systems herein disclosed.

DETAILED DESCRIPTION

Figure 1:
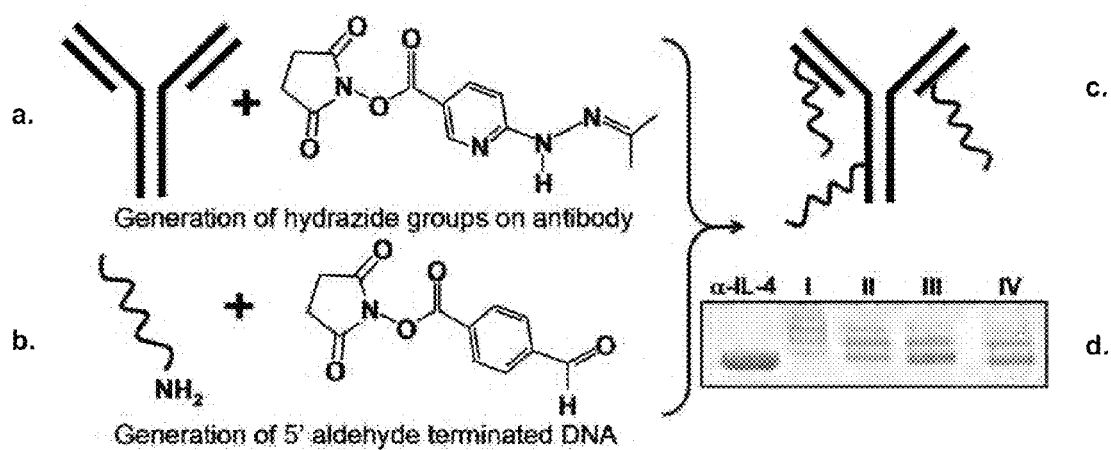
FIG. 1 is a schematic illustration of a coupling strategy utilized to prepare polynucleotide-encoded-protein herein disclosed. Panel a is a schematic illustration of a reaction for the preparation of an antibody; Panel b is a schematic illustration of a reaction the preparation of a polynucleotide; Panel c is an illustration of the polynucleotide-encoded antibody resulting from the conjugation of the antibody shown in Panel a and the polynucleotide shown in Panel b; Panel d shows a gel mobility shift assay showing that the number of polynucleotide strand A1' attached to the antibody can be controlled by adjusting the amount of coupling molecule to antibody as shown in Panel a. Here, lanes I-IV corresponds to stoichiometric ratios of 300:1, 100:1, 50:1, 25:1 of the coupling molecule to antibody respectively.

Methods and systems for the detection of targets in a sample are disclosed. In the methods and systems herein disclosed polynucleotide-encoded proteins are used in combination with substrate polynucleotides to detect one or more targets in a sample.

The term "detect" or "detection" as used herein indicates the determination of the existence, presence or fact of a target or signal in a limited portion of space, including but not limited to a sample, a reaction mixture, a molecular complex and a substrate. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

The term "target" as used herein indicates an analyte of interest. The term "analyte" refers to a substance, compound or component whose presence or absence in a sample has to be detected. Analytes include but are not limited to biomolecules and in particular biomarkers. The term "biomolecule" as used herein indicates a substance compound or component associated to a biological environment including but not limited to sugars, aminoacids, peptides proteins, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state.

The term "sample" as used herein indicates a limited quantity of something that is indicative of a larger quantity of that something, including but not limited to fluids from a biological environment, specimen, cultures, tissues, commercial recombinant proteins, synthetic compounds or portions thereof.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Accordingly, the term polynucleotide includes nucleic acids of any length DNA RNA analogs and fragments thereof. A polynucleotide of three or more nucleotides is also called nucleotidic oligomers or oligonucleotide.

The term "polypeptide" as used herein indicates an organic polymer composed of two or more amino acid monomers and/or analogs thereof. The term "polypeptide" includes amino acid polymers of any length including full length proteins and peptides, as well as analogs and fragments thereof. A polypeptide of three or more amino acids is also called a protein oligomer or oligopeptide. As used herein the term "amino acid", "amino acidic monomer", or "amino acid residue" refers to any of the twenty naturally occurring amino acids including synthetic amino acids with unnatural side chains and including both D an L optical isomers. The term "amino acid analog" refers to an amino acid in which one or more individual atoms have been replaced, either with a different atom, isotope, or with a different functional group but is otherwise identical to its natural amino acid analog.

The term "protein" as used herein indicates a polypeptide with a particular secondary and tertiary structure that can participate in, but not limited to, interactions with other biomolecules including other proteins, DNA, RNA, lipids, metabolites, hormones, chemokines, and small molecules.

The term "antibody" as used herein refers to a protein that is produced by activated B cells after stimulation by an antigen and binds specifically to the antigen promoting an immune response in biological systems and that typically consists of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab Fv, Fab' F(ab')2 and the like. A monoclonal antibody is an antibody that specifically binds to and is thereby defined as complementary to a single particular spatial and polar organization of another biomolecule which is termed an "epitope". A polyclonal antibody refers to a mixture of monoclonal antibodies with each monoclonal antibody binding to a different antigenic epitope. Antibodies can be prepared by techniques that are well known in the art, such as immunization of a host and collection of sera (polyclonal) or by preparing continuous hybridoma cell lines and collecting the secreted protein (monoclonal).

The wording "specific" "specifically" or specificity" as used herein with reference to the binding of a molecule to another refers to the recognition, contact and formation of a stable complex between the molecule and the another, together with substantially less to no recognition, contact and formation of a stable complex between each of the molecule and the another with other molecules. Exemplary specific bindings are antibody-antigen interaction, cellular receptor-ligand interactions, polynucleotide hybridization, enzyme substrate interactions etc. The term "specific" as used herein with reference to a molecular component of a complex, refers to the unique association of that component to the specific complex which the component is part of. The term "specific" as used herein with reference to a sequence of a polynucleotide refers to the unique association of the sequence with a single polynucleotide which is the complementary sequence.

The wording "polynucleotide-encoded protein" refers to a polynucleotide-protein complex comprising a protein component that specifically binds to, and is thereby defined as complementary to, a target and an encoding polynucleotide attached to the protein component. In some embodiments, the encoding polynucleotide attached to the protein is protein-specific. Those embodiments can be used to perform assays that exploit the protein-specific interaction to detect other proteins, cytokines, chemokines, small molecules, DNA, RNA, lipids, etc., whenever a target is known, and sensitive detection of that target is required.

The term "polynucleotide-encoded antibody" as used herein refers to a polynucleotide-encoded protein wherein the protein component is an antibody.

The term "attach" or "attached" as used herein, refers to connecting or uniting by a bond, link, force or tie in order to keep two or more components together, which encompasses either direct or indirect attachment such that for example where a first molecule is directly bound to a second molecule or material, and the embodiments wherein one or more intermediate molecules are disposed between the first molecule and the second molecule or material.

The wording "substrate polynucleotide" as used herein refers to a polynucleotide that is attached to a substrate so to maintain the ability to bind to its complementary polynucleotide. A substrate polynucleotide can be in particular comprised of a sequence that specifically binds and is thereby defined as complementary with an encoding-polynucleotide of a polynucleotide encoded protein.

The term "substrate" as used herein indicates an underlying support or substratum. Exemplary substrates include solid substrates, such as glass plates, microtiter well plates, magnetic beads, silicon wafers and additional substrates identifiable by a skilled person upon reading of the present disclosure.

In the polynucleotide-encoded proteins herein disclosed each protein specifically binds to, and is thereby defined as complementary to, a pre-determined target, and each encoding polynucleotide-specifically binds to, and is thereby defined as complementary to, a pre-determined substrate polynucleotide.

In embodiments wherein the protein is an antibody, the protein-target interaction is an antibody-antigen interaction. In embodiments wherein the protein is other than an antibody, the interaction can be receptor-ligand, enzyme-substrate and additional protein-protein interactions identifiable by a skilled person upon reading of the present disclosure. For example, in embodiments where the protein is streptavidin, the protein-target interaction is a receptor-ligand interaction, where the receptor is streptavidin and the ligand is biotin, free or attached to any biomolecules.

Additionally, in the methods and systems herein disclosed each substrate polynucleotide and encoding polynucleotide is bindingly distinguishable from another. In some embodiments of the methods and systems herein disclosed, each substrate polynucleotide of a substrate is sequence specific and positionally distinguishable from another.

The wording "bindingly distinguishable" as used herein with reference to molecules, indicates molecules that are distinguishable based on their ability to specifically bind to, and are thereby defined as complementary to a specific molecule. Accordingly, a first molecule is bindingly distinguishable from a second molecule if the first molecule specifically binds and is thereby defined as complementary to a third molecule and the second molecule specifically binds and is thereby defined as complementary to a fourth molecule, with the fourth molecule distinct from the third molecule.

The wording "positionally distinguishable" as used herein refers to with reference to molecules, indicates molecules that are distinguishable based on the point or area occupied by the molecules. Accordingly, positionally distinguishable substrate polynucleotides are substrate polynucleotide that occupy different points or areas on the substrate and are thereby positionally distinguishable.

The polynucleotide-encoded protein herein disclosed can be produced with common bioconjugation methods, such as chemical cross-linking which include techniques relying on the presence of primary amines in the protein to be bound (usually found on Lysine residues). In particular, polynucleotide-encoded-protein can be produced by the covalent conjugation strategy shown in FIGS. 1 and 2 for polynucleotide-encoded antibodies (FIG. 1) and a polynucleotide-encoded streptavidin (FIG. 2).

In the embodiment illustrated in FIG. 1, 5'-aminated polynucleotides are coupled to the antibody via a hydrazone linkage (Kozlov, I. A.; Melnyk, P. C.; Stromsborg, K. E.; Chee, M. S.; Barker, D. L.; Zhao, C. *Biopolymers* 2004, 73, 621-630), as schematically illustrated in FIG. 1 and exemplified in Example 1.

Figure 2:
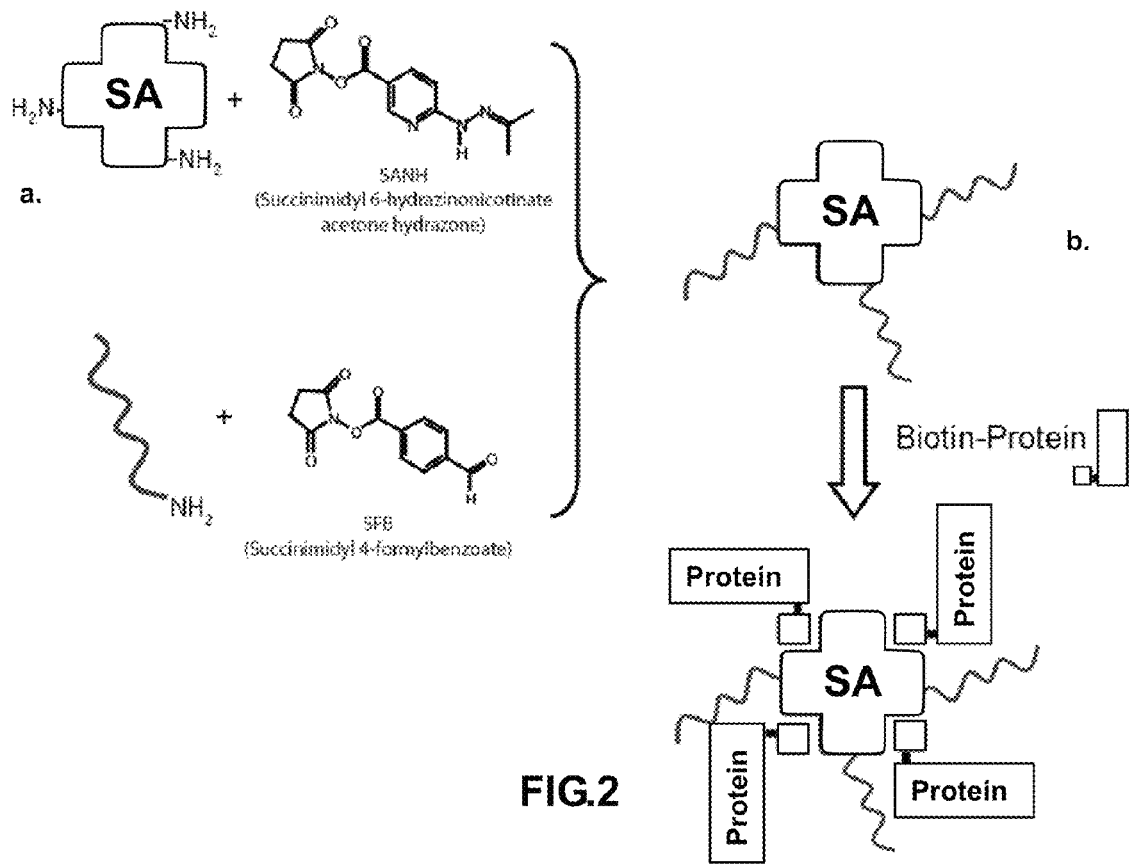
FIG. 2 is a schematic illustration of the conjugation chemistry of a polynucleotide-encoded protein disclosed herein. Panel a shows a schematic illustration of the conjugation chemistry between a polynucleotide and the protein streptavidin; Panel b shows the assembly of the polynucleotide-encoded streptavidin with a protein containing biotin, which is the ligand of streptavidin; SA indicates the streptavidin protein, Biotin-Protein: indicates a protein containing the ligand biotin.

Identical bioconjugation chemistry can be used for the production of any polynucleotide-encoded-protein such as polynucleotide-encoded streptavidin, as exemplified in Example 2 and illustrated in FIG. 2.

The number of encoding polynucleotides to be conjugated with a particular polynucleotide-encoded protein can be varied. In particular, the number of polynucleotides attached to the protein component can be modulated to minimize the size and therefore the steric hindrance of the pending moieties while still maintaining binding specificity. The optimization can be performed by way of procedures exemplified in Example 3 and illustrated in the related in FIG. 3. In Example 3 and FIG. 3, different batches of polynucleotide-encoded antibodies were made, in which the total number of polynucleotides linked to each antibody were varied. Because the encoding polynucleotides of FIG. 3 and Example 3 contained a fluorophore, the binding efficiency of each variant for cell surface markers could be tested out using FACS. It should be noted that there are other analogous techniques to measure and optimize antibody binding affinity as a function of polynucleotide loading, including techniques which directly measure the binding kinetics of antibodies such as surface plasmon resonance (SPR) and isothermal titration calorimetery (ITC).

In some embodiments, the number of encoding polynucleotides to be attached to each protein can be any from 1 to 6. In some embodiments, such as cell sorting, attaching 3 encoding polynucleotides per protein provides the further advantage of minimizing the steric effects of labeling and therefore allowing a labeling of a polynucleotide-encoded protein with a plurality of encoding polynucleotides for high affinity hybridization with the complementary substrate polynucleotide.

The length of the polynucleotide forming the pending moieties can also be controlled to optimize binding of the polynucleotide-encoded protein to the substrate. In particular, the length of the encoding polynucleotides can be optimized for orthogonalization purposes as illustrated in Example 8 and FIG. 9 and further discussed below.

In the following detailed description reference will be often made to embodiments wherein the polynucleotide-encoded protein is a polynucleotide-encoded antibody. A skilled person will be able to adapt the teaching provided for the polynucleotide-encoded antibodies to other polynucleotide-encoded proteins upon reading of the present disclosure.

The substrate polynucleotides can be produced by normal techniques in the field. For example, first the polynucleotides can be chemically synthesized. The polynucleotides can then be pin spotted according the paradigm outlined by Pat Brown at Stanford (Schena M, Shalon D, Davis R W, Brown P O. *Science*. 1995 Oct. 20; 270(5235): 467-70). The substrate polynucleotides so produced can be then attached to a substrate according to techniques identifiable by a skilled person upon reading of the present disclosure. Particularly, suitable polynucleotides for the production of substrate polynucleotides include at least 75 mers long on polylysine substrates.

In some embodiments, the encoding polynucleotides and/or the substrate polynucleotides are orthogonalized to minimize the non-specific binding between encoding-polynucleotide and substrate polynucleotide. Accordingly, orthogonalized polynucleotides include polynucleotides whose sequence is computationally generated to minimize incomplete base pairing, metastable states and/or other secondary structures to minimize non specific interactions between polynucleotides and non linear secondary interactions in the polynucleotide usually associated with random generation of the relevant sequences.

The term "orthogonalization" as used herein refers to the process by which a set of polynucleotides are generated computationally, in which incomplete base pairing, metastable states and other secondary structures are minimized, such that a polynucleotide only binds to its complementary strand and none other. Exemplary orthogonalization techniques used in this disclosure include orthogonalization performed according to the paradigm outlined by Dirks et al. (Dirks, R. M.; Lin, M.; Winfree, E.; Pierce, N. A. *Nucleic Acids Research* 2004, 32, (4), 1392-1403)

In particular, in some embodiments, the encoding-polynucleotides and the corresponding complementary substrate polynucleotides are orthogonalized polynucleotides having the sequences from SEQ ID NO: 7 to SEQ ID NO 18 (see Example 8 and related Table 1)

Figure 9:
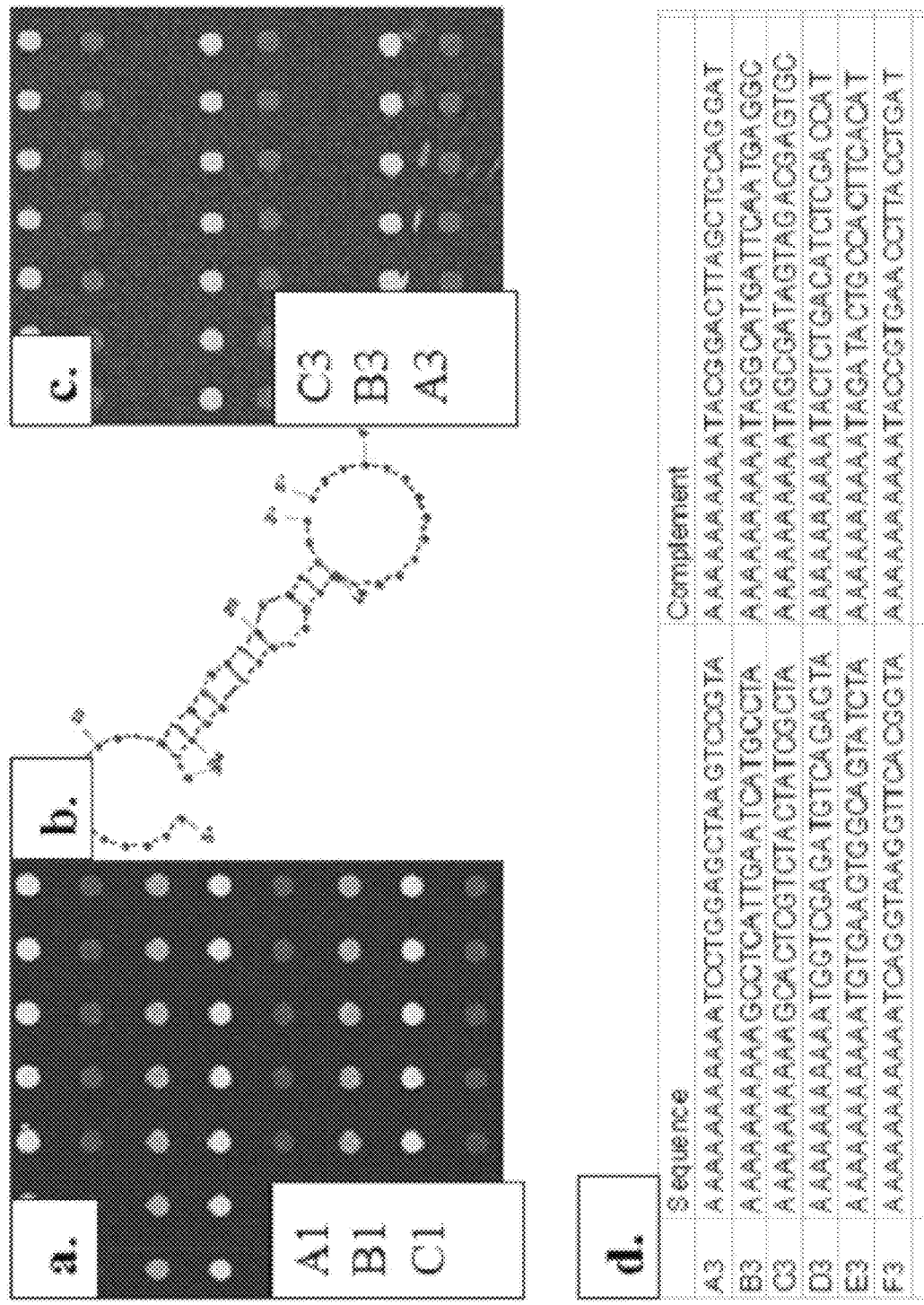
FIG. 9 illustrates the results of the in silico orthogonalization of substrate polynucleotides wherein each substrate polynucleotide is orthogonal to the others and bind to their corresponding antibody specific polynucleotides. Panel a. shows a glass slide printed with three substrate polynucleotides exposed to two polynucleotide-encoded antibodies complementary to two out of the three substrate polynucleotides; Panel b shows the secondary structure formed from the hybridization of A1 in silico hybridization in silico of the two substrate polynucleotides complementary to the antibody specific polynucleotide; Panel c shows generation in silico of additional substrate polynucleotide with the constraints that each strand be orthogonal with each other and with their corresponding complements; Panel d shows a set of 6 orthogonal sequences, listed 5' to 3' end.

Additional orthogonalized polynucleotides can be further identified by way of methods and procedures, such as in silico orthogonalization (i.e. computerized orthogonalization) of polynucleotides exemplified in Example 8 and illustrated in FIG. 9, and additional procedures that would be apparent to a skilled person upon reading of the present disclosure.

The methods and systems herein disclosed can be used for performing assays for the detection of targets, including mono-parameter assays, and multiparameter assays, all of which can be performed as multiplex assays.

The term "monoparameter assay" as used herein refers to an analysis performed to determine the presence, absence, or quantity of one target. The term "multiparameter assay" refers to an analysis performed to determine the presence, absence, or quantity of a plurality of targets. The term "multiplex" or "multiplexed" assays refers to an assay in which multiple assays reactions, e.g., simultaneous assays of multiple analytes, are carried out in a single reaction chamber and/or analyzed in a single separation and detection format.

In some embodiments, the methods and systems herein disclosed can advantageously used to perform diagnostic assays, wherein the target(s) to be detected are predetermined biomarkers associated with a predetermined disease. Those embodiments are particularly advantageous in a diagnostic approach where different classes of biomaterials and biomolecules are each measured from a different region of a typically heterogeneous tissue sample, thus introducing unavoidable sources of noise that are hard to quantitate.

Figure 4:
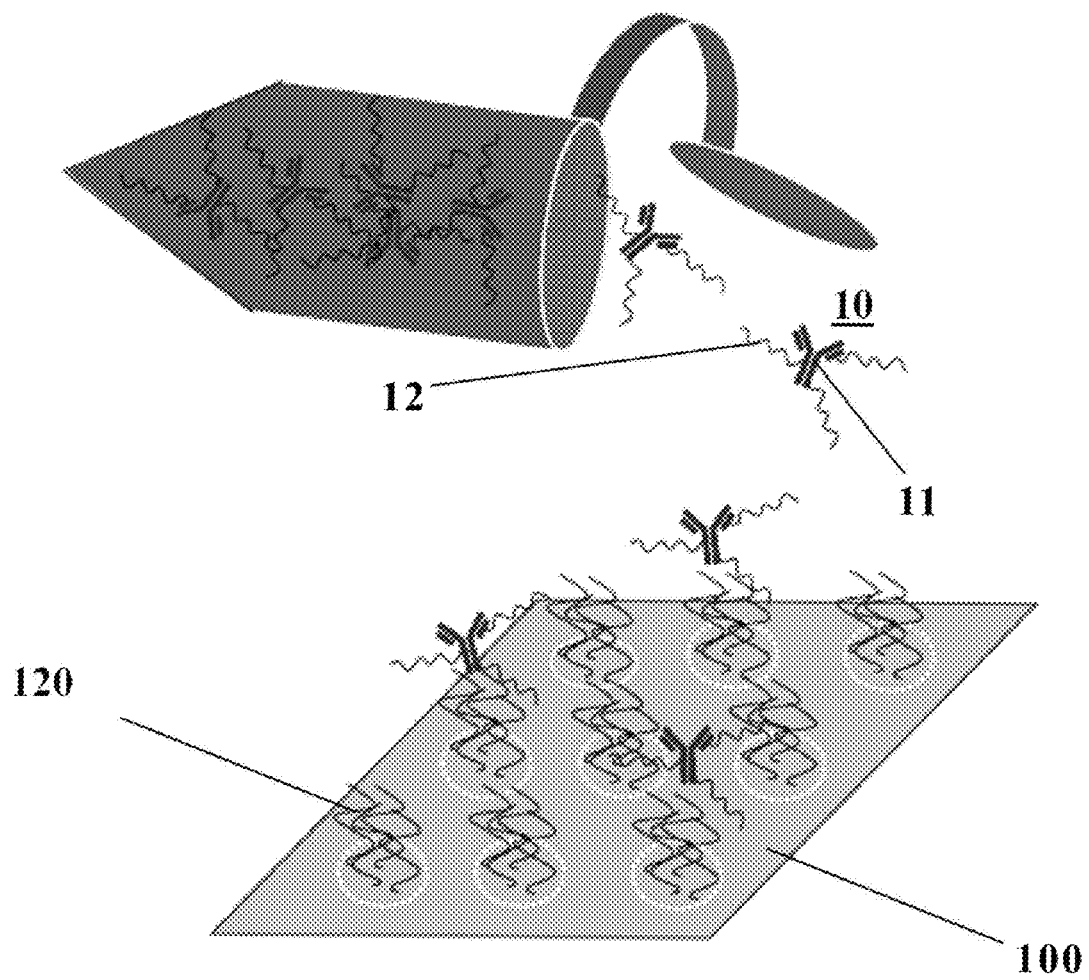
FIG. 4. is a schematic illustration of a combined use of polynucleotide-encoded antibodies and substrate polynucleotides herein disclosed.

In some embodiments of the methods and systems herein disclosed, the polynucleotide-encoded protein and substrate polynucleotide are used in combination as schematically illustrated in FIG. 4 wherein the polynucleotide-encoded proteins are polynucleotide-encoded antibodies.

In the embodiment of FIG. 4, a polynucleotide-encoded antibody (10) is provided in combination with a substrate (100). The polynucleotide-encoded antibody (10) is comprised of an antibody (11) and an encoding-polynucleotide (12). The substrate (100) has a substrate polynucleotide (120) bound to a substrate surface. The encoding polynucleotide (12) is complementary to the substrate polynucleotide (120) so that when contacted the substrate polynucleotide (120) and the encoding polynucleotide (12) hybridize.

In the embodiment shown in FIG. 4 the polynucleotide-encoded antibodies herein disclosed form a protein array that can be contacted with a sample to detect a target in the sample. The embodiment of FIG. 4 is particularly advantageous for detecting and/or sorting protein-targets.

In additional embodiments, particularly suitable for detecting and/or sorting cells targets, some or all of the polynucleotide-encoded antibodies are contacted with the sample before contacting the polynucleotide-encoded-antibodies with the complementary substrate polynucleotide. In those additional embodiments, the antibodies and the one or more corresponding targets can bind in absence of the substrate, e.g., in a solution phase, where both molecules have a complete orientational freedom and the access of the target to the binding pocket of the antibody is not impaired by the substrate. Additionally, surface-induced protein denaturation does not occur because the polynucleotide-encoded antibodies remain in solution preserving the tertiary fold of the protein. In addition, biofouling is minimized (see also description below), so that the sensitivity and specificity of the performed assay is improved as well as the detectability of the antibody target complex bound to the substrate, when compared to corresponding methods and system of the art. Exemplary embodiments showing some of the above advantages are illustrated in FIGS. 5, 7, 8 11 and 13.

In the methods and systems herein disclosed the antibody-target complex bound to the substrate is eventually detected from the substrate.

In some embodiments, detection of the complex is performed by providing a labeled molecule, which includes any molecule that can specifically bind a polynucleotide-encoded-protein target complex to be detected (e.g. an antibody, aptamers, peptides etc) and a label that provides a labeling signal, the label compound attached to the molecule. The labeled molecule is contacted with the polynucleotide-encoded protein-target complex and the labeling signal from the label compound bound to the polynucleotide-encoded protein-target complex on the substrate can then be detected, according to procedure identifiable by a skilled upon reading of the present disclosure and, in particular, of the Examples section.

In embodiments wherein one or more targets and/or a plurality of targets is detected described below in more details, the labeled molecule can be formed of a plurality of labeled molecules. Each labeled molecules comprises a molecule that specifically binds one target of the one or more targets/plurality of targets and a label compound attached to the molecule, the label compound providing a labeling signal, each labeled molecule detectably distinguishable from another.

The wording "detectably distinguishable" as used herein with reference to labeled molecule indicates molecules that are distinguishable on the basis of the labeling signal provided by the label compound attached to the molecule. Exemplary label compounds that can be use to provide detectably distinguishable labeled molecules, include but are not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and additional compounds identifiable by a skilled person upon reading of the present disclosure.

In some embodiments, the plurality of labeled molecules is contacted with the plurality of polynucleotide-encoded protein-target complexes for a time and under condition to allow binding of the plurality of polynucleotide-encoded protein-target complexes with the plurality of labeled molecules. The labeling signal is then detected from the plurality of labeled molecules bound to the plurality of polynucleotide-encoded protein-target complexes on the substrate.

In some embodiments, the detection method can be carried either via fluorescent based readouts, in which the labeled antibody is labeled with fluorophore which includes but not exhaustively small molecular dyes, protein chromophores, quantum dots, and gold nanoparticles. In particular, in some embodiments, in any of the methods and systems herein disclosed, detection can be carried out on gold nanoparticle-labeled secondary detection systems in which a common photographic development solution can amplify the gold nanoparticles as further described below. Also, if the readout comes from dark field scattering of gold particles, single molecule digital proteomics is enabled. Additional techniques are identifiable by a skilled person upon reading of the present disclosure and will not be further discussed in details.

The terms "label" and "labeled molecule" as used herein as a component of a complex or molecule refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence the wording and "labeling signal" as used herein indicates the signal emitted from the label that allows detection of the label, including but not limited to radioactivity, fluorescence, chemolumiescence, production of a compound in outcome of an enzymatic reaction and the likes.

In some embodiments, one specific target is detected. In those embodiments contacting the polynucleotide-encoded antibodies with the target can be performed before or after contacting the polynucleotide-encoded antibody with the substrate.

The embodiments wherein contacting the polynucleotide antibodies with the target is performed before contacting the polynucleotide-encoded antibody with the substrate are particularly suitable to sort or detect cells. In those embodiments, the efficiency and specificity of the binding between antibody and target is maximized even for a detection of a single target. A possible, although non binding, explanation is that in the methods and system herein disclosed the target capture is not driven by antibody to cell surface marker interactions, but rather by the increased avidity of antibody specific polynucleotide for the corresponding strands on the microarray through cooperative binding, greatly increasing capture efficiency. This advantage is particularly relevant for target cells that can be efficiently captured so that with this process it is typical to see a DNA spot entirely occupied by a confluent layer of cells. (see Example 5 and FIG. 5).

The embodiments wherein contacting the polynucleotide-encoded antibodies with the target is performed after contacting the polynucleotide-encoded antibody with the substrate are particularly suitable to sort or detect proteins with high sensitivity. Exemplary embodiments of methods and systems herein disclosed wherein contacting the polynucleotide-encoded antibodies with the target is performed after contacting the polynucleotide-encoded antibody with the substrate are exemplified in Examples 12, and 13 and illustrated in FIGS. 15, 19, 20, 21, 22, 23, 24(*c*). In those embodiments, competition for the same specific substrate polynucleotide between a polynucleotide-encoded-proteins bound to the target and polynucleotide-encoded-proteins not bound to the target can be eliminated and the sensitivity of the assay consequently increased. Further, in those embodiments the concentration of polynucleotides on the substrate can be optimized so that higher concentration of polynucleotide-encoded proteins can be bound to the substrate, which will in turn result in higher concentrations of correctly assembled complex, which in turn increase the overall detection sensitivity, by virtue of equilibrium thermodynamics law that govern each binding.

Figure 5:
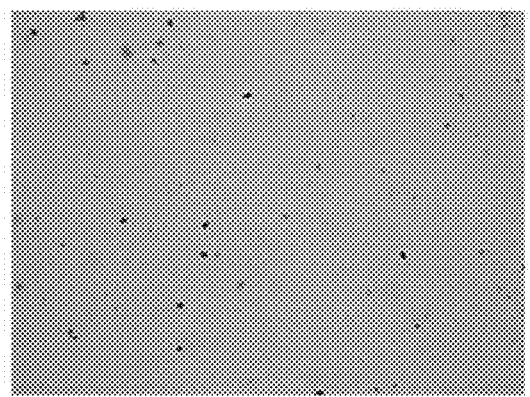
FIG. 5 illustrates an embodiment of the methods and systems wherein the polynucleotide-encoded protein is based on the streptavidin biotin system and the targets are cells. Panel a shows assembly of the polynucleotide-encoded streptavidin according to FIG. 2, wherein the biotin containing protein is the Major histocompatibility complex (MHC) and preassembly of the polynucleotide-encoded straptavidin onto the substrate before the cells of interest are exposed to the glass substrate. Panel b shows exposure of the microarray following binding of the polynucleotide-encoded MHC to the cells in solution.
Figure 5:
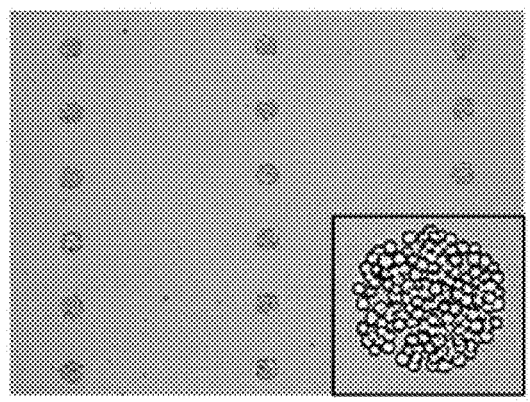

Monoparameter assays that can be performed with the methods and systems exemplified in FIGS. 4 and 5 and in Example 5, include but are not limited to, any assays for the detection of single markers in serum, single protein detection in biological samples, cell sorting according to one surface marker and further assays identifiable by a skilled person upon reading of the present disclosure.

Figure 6:
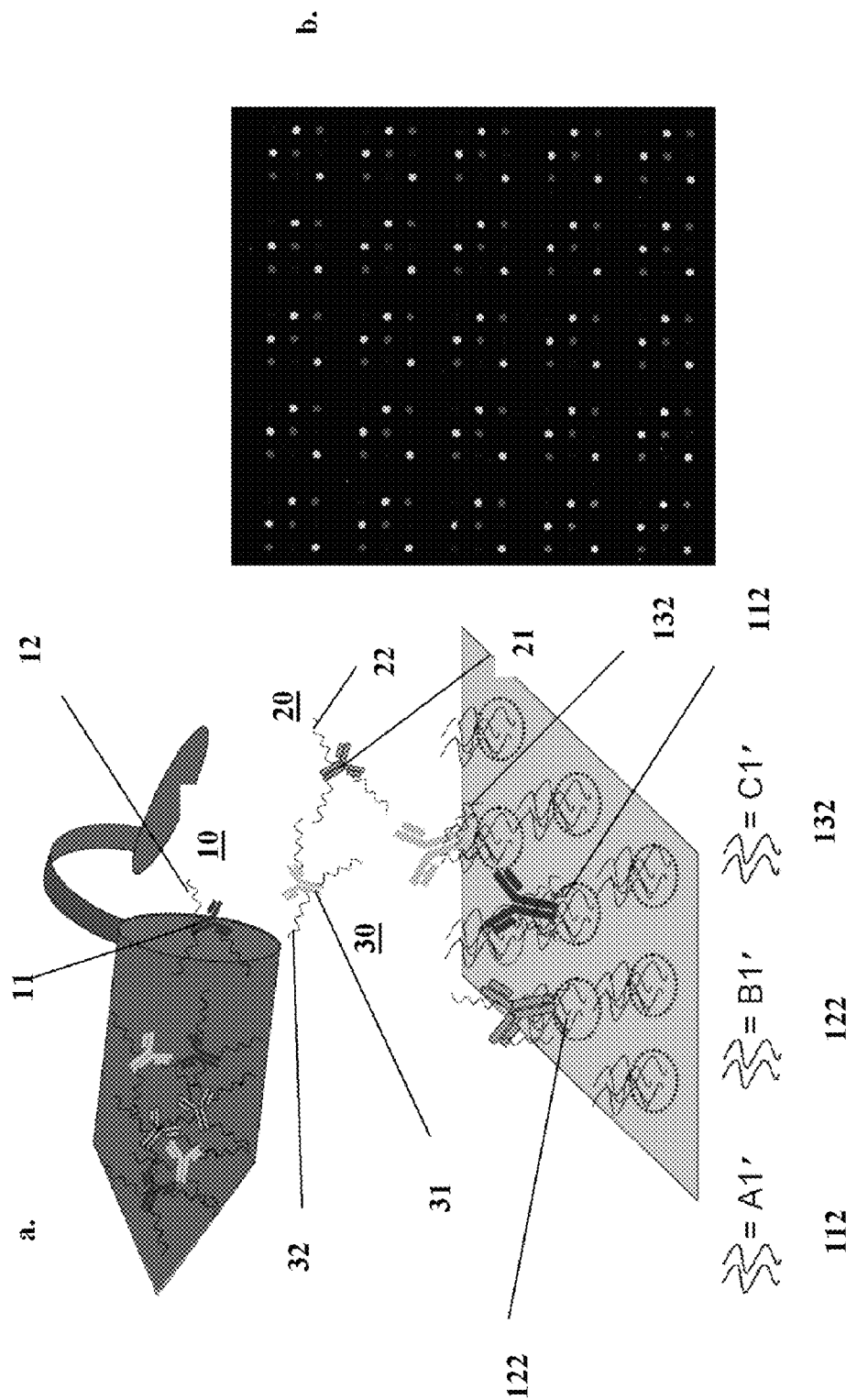
FIG. 6 illustrates a method of detecting a plurality of targets using polynucleotide-encoded antibodies and substrate polynucleotide herein disclosed. Panel a shows a schematic illustration of a combined used of a plurality of polynucleotide-encoded antibodies herein disclosed in combination with substrate polynucleotides Panel b shows a related immunoassay performed using polynucleotide-encoded antibodies and substrate polynucleotide herein disclosed.

In some embodiments, detection of a plurality of targets is performed, according to a strategy schematically illustrated in FIG. 6.

A plurality of polynucleotide-encoded antibodies (10, 20 and 30) is produced, each polynucleotide-encoded antibody able to specifically bind to a predetermined target with the antibody component (11, 21 and 31) and to bind to a complementary substrate polynucleotide with the encoding-polynucleotide component. (12, 22 and 32). A substrate is generated with sequence specific positionally distinguishable substrate polynucleotides (112, 122, and 132).

The polynucleotide-encoded antibodies (10), (20) and (30) are then contacted with the substrate polynucleotide (112), (122) and (132) and upon binding of the antibody specific polynucleotide with the corresponding substrate polynucleotide, polynucleotide-encoded antibody complexes self assemble on the substrate.

In the embodiment shown in FIG. 6, a protein array composed of a plurality of bindingly distinguishable and positionally distinguishable antibodies is produced. Those embodiments are particularly advantageous for sorting and/or detecting different protein-targets with a high sensitivity. Exemplary illustrations of those embodiments are shown in Examples 9, 10 and 12 and in FIGS. 10, 12, 13 and 15*a*.

In additional embodiments, the plurality of polynucleotide-encoded antibodies is contacted with a sample for detection of the related target before contacting the substrate polynucleotides. In those embodiments, the methods and systems herein disclosed can be used to perform multiplexed multiparameter assays wherein due to the improved sensitivity and selectivity associated with binding of antibody and target in absence of a substrate and in view of the reduced biofouling and protein denaturation, a large number of biomarkers can be efficiently detected in a quantitative and/or qualitative fashion. Exemplary illustrations of those embodiments are shown in Examples 9, 10 and 12 and in FIGS. 10, 12, 13 and 15.

Multiparameter assays that can be performed with the methods and systems exemplified in Examples 9, 10 and 12 and illustrated in FIGS. 10, 12, 13 and 15 include but are not limited to any proteomic analysis, tissue analysis, serum diagnostics, biomarker, serum profiling, multiparameter cell sorting, single cell studies, and additional assays identifiable by a person skilled in the art upon reading of the present disclosure.

In some embodiments, the combined use schematically illustrated in FIG. 6 can be applied in a method for sorting a plurality of targets which is particularly advantageous when the plurality of targets is composed of different types of cells, and in particular primary cells. In those embodiments, the polynucleotide-encoded antibody is preferably contacted with the sample including the cells before contacting the substrate according to procedure exemplified in Example 9 and illustrated in FIG. 10.

Embodiments of the methods and systems wherein the plurality of targets is composed of different types of cells are particularly advantageous over corresponding methods and systems of the art such as panning in which cells interact with surface marker-specific antibodies printed onto an underlying substrate (Cardoso, A. A.; Watt, S. M.; Batard, P.; Li, M. L.; Hatzfeld, A.; Genevier, H.; Hatzfeld, J. *Exp. Hematol.* 1995, 23, 407-412). In particular, the efficiency of cell capture on the substrate is improved with respect to prior art methods and systems, due to the use of polynucleotide to bind the antibody to the substrate (see FIG. 5 and FIG. 10). Additionally, those preferred embodiments do not have the same limitations as conventional spotted protein microarrays, such as antibodies that are not always oriented appropriately on a surface, and/or antibodies that can dry out and lose functionality.

Any of the embodiments to sort cells has several advantages over methods and systems to sort cells known in the art such as FACS, since the cells sorted by the methods and systems herein disclosed are immediately available for post-sorting analysis of gene and/or protein expression. In addition, the methods and systems herein disclosed perform a spatially multiplexed sorting of multiple cells that is particularly effective in sorting cells according to multiple cells surface markers and is not limited by the number of spectrally distinct fluorophores that can be utilized to label the cell surface markers used for the sorting, as exemplified in Example 9 and related FIG. 10.

Figure 11:
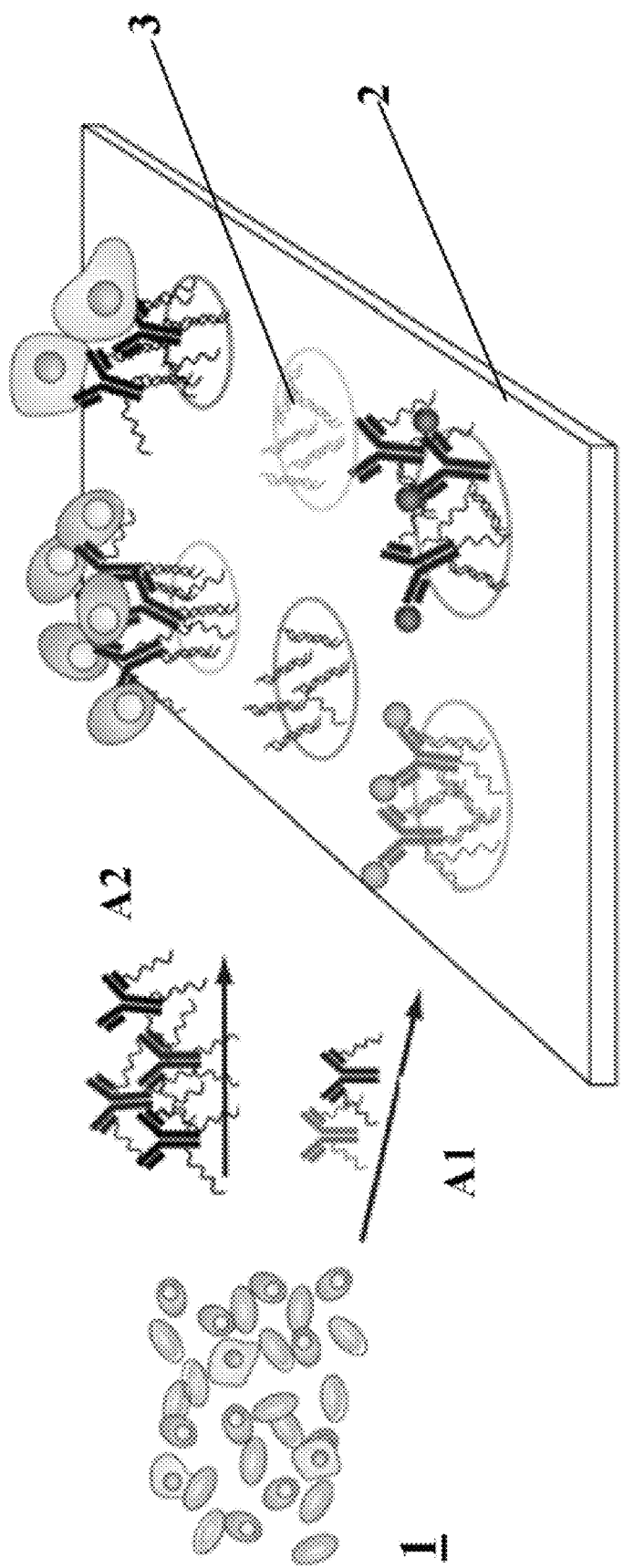
FIG. 11 is a schematic illustration of a combined use of polynucleotide-encoded antibodies and substrate polynucleotides herein disclosed for cell sorting and/or co-detection of chemically distinct molecules.

In some embodiments the combined use depicted in FIG. 6 can be applied to detection of a plurality of chemically distinct targets according to the approach schematically illustrated in FIG. 11. In particular, the approach is illustrated for separation of a plurality of distinct biomarkers such as DNA cells and proteins. In the embodiment illustrated in FIG. 11, the methods and systems herein disclosed are performed to separate cells (1) (see FIG. 11, arrow A1) and analyze the relevant genomic and proteomic signature (see FIG. 11, arrow A2) using a substrate (2) with a plurality of substrate polynucleotides (3) attached thereto in a multiparameter assay for the analysis of cells, genes and proteins.

In some of those embodiments, the sample is contacted with a plurality of polynucleotide-encoded antibodies to allow formation of a plurality of polynucleotide-encoded biomarker complexes that are then contacted to a substrate such as a DNA array wherein the antibody specific polynucleotides specifically bind the corresponding DNA strands. In some embodiments, where detection of a target polynucleotide is desired, a labeled polynucleotide that specifically bind to the target polynucleotide can further be contacted with the sample for the production of a labeled target polynucleotide that specifically binds a predetermined DNA strands on the substrate. The labeled target polynucleotide is eventually contacted with the substrate polynucleotide and detected. According to this approach, the cells, protein and DNA biomarkers are sorted and then detected in a single substrate, thus allowing advantageous performance of multiplexed multiparameter assays.

In those embodiments, by using polynucleotides as a common assembly strategy for cells, cDNAs, and proteins, it is possible to optimize the substrate conditions for high DNA loading onto the spotted substrates, and for complementary DNA loading on the antibodies. This and the reduced biofouling associated with polynucleotide based binding of antibodies on the substrate, allows performance of highly sensitive sandwich assays for protein detection, as well as high efficiency cell sorting (compared with traditional panning). An exemplary method and system to perform detection of chemically different biomarkers is described in Example 10 and illustrated in FIG. 13.

Assays to sort targets performable with the methods and systems exemplified in Examples 9, 10, 12 and 13 and illustrated in FIGS. 13, 10c, 10d 15a, 22, 23, 24, include any assay that requires detection of a particular target (including but not limited to cell targets, protein-target or gene targets) in a mixture, which will be identifiable by a skilled person upon reading of the present disclosure.

In some embodiments, high sensitivity detection of single or multiple targets can be performed by using antibodies labeled with metal nanoparticles for the detection, followed by electroless metal deposition.

In those embodiments, any of the methods and systems herein disclosed can be performed by using a metal nanoparticle (in particular Au nanoparticles) as a labeling molecule to detect the encoded-polynucleotide protein-target complex bound to the substrate. In particular, a metal nanoparticle, such as a gold nanoparticle, is conjugated to the labeled molecule (e.g., a second antibody) used for labeling the polynucleotide-encoded protein-target complex bound to the substrate. Metal particles, such as Au nanoparticles, have unique optical properties in that a particle that is much smaller than the wavelength of visual light can still be readily imaged using light scattering. This allows for an immunoassay to be read out by counting the nanoparticle labels (and hence the proteins) using a light scattering microscope. This approach is herein also defined as digital method or digital DEAL—the counted number of particles represents the absolute number of proteins captured via specific antibodies, with the assumption that each nanoparticle corresponds to a single protein.

Figure 16:
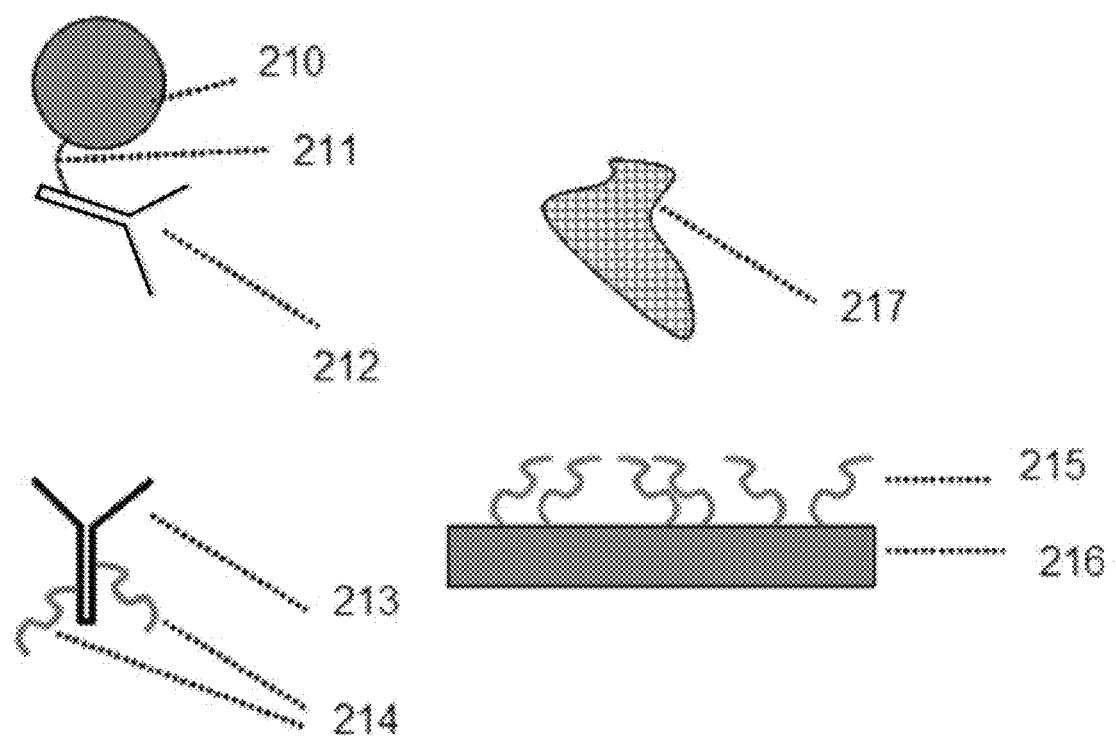
FIG. 16 is a schematic illustration of a combined use of polynucleotide-encoded antibodies and substrate polynucleotides wherein the polynucleotide-encoded antibodies are labeled with metal nanoparticles according to an embodiment of the methods and systems herein disclosed.
Figure 17:
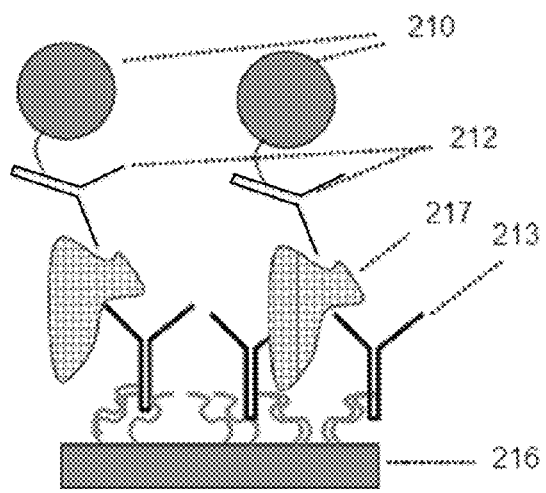
FIG. 17 is an additional schematic illustration of the combined use of FIG. 16, showing the polynucleotide-encoded antibody target complex bound to the substrate and labeled with metal nanoparticles according to an embodiment of the methods and systems herein disclosed.

FIGS. 16 and 17 show schematically an exemplary embodiment of the methods and systems herein disclosed, wherein the labeling molecule includes a metal nanoparticle such as a gold nanoparticle. In particular, a gold nanoparticle (210) is attached via a linker molecule (211) onto a 2° antibody (212). On the 1° AB (213) one or more ssDNA oligomers (214) are attached. The target to be detected (217) is in a solution or biological environment. The assay itself will be measured on a surface (216) that has been coated with ssDNA' (215). Exemplary embodiments are further illustrated in FIGS. 18 to 22 and exemplified in Example 13.

An advantage of some embodiments of the methods and systems herein disclosed when metal nanoparticles are used for labeling is that there is no need to calibrate the immunoassay each time a protein measurement is done, since amount of protein counted represents an absolute measurement. Fluorescence or absorbance assays, by comparison, represent relative measurements, since they are dependent upon background fluorescence (absorbance) levels, light amplification electronics, photobleaching effects (for fluorescence), etc. The nanoparticle-based digital methods and systems herein disclosed can be advantageously used for: (1) the ultrasensitive detection of proteins at high attoMolar levels ($10^3$-$10^6$ fold improvement over conventional ELISA immunoassays) and over a broad concentration range; (2) the multiplexed detection of several proteins on the same chip; and (3) the detection of extracellular signaling molecules, cytokines, in human patient sera.

Some embodiments of the methods and systems herein disclosed wherein labeling and detection is performed by using metal nanoparticles is based on a detection system, such as a Raleigh scattering mechanism that allows for the indirect visualization of individual plasmonic nanoparticles, in this case 40 nm Au nanoparticles, that are conjugated to detection antibodies to realize single protein counting. A graphical software interface can be utilized to digitally count the absolute number of particles and to thus quantitate the amount of proteins. Those embodiments are in sharp contrast to conventional quantitation methods using averaged signal readout after amplification. In conjunction with the DNA encoded antibody library technique, the methods and systems herein disclosed that use metal nanoparticles as label compounds are able to multiplex the detection by simultaneously counting different kinds of proteins from the same biological sample.

A further advantage of the methods and systems herein disclosed wherein metal nanoparticles are used as label compounds over highly sensitive protein detection techniques of the art that are based upon variants of the ELISA scheme are the possibility to eliminate an amplification of the signal and associated additional noise and time required for performance. The prior art methods all require some sort of amplification step, and each method requires some level of calibration that must be carried out for every assay performed. For example, methods in which the 2° AB is labeled with DNA, and that DNA is amplified using the polymerase chain reaction (PCR) have been reported. It is this amplified DNA that is detected and then correlated to the measured protein concentration. In another variant, the 2° AB is labeled with a gold nanoparticle, and then silver metal is deposited (via electroless deposition) onto that gold nanoparticle in order to generate an amplified absorbance signal. For both of those cases, the amplification step itself introduces noise into the assay, and requires an additional amount of time—often a significant amount of time.

An additional advantage of the methods and systems herein disclosed that use metal nanoparticles over the above mentioned prior art methods is that none of the prior art methods are digital—meaning none of those methods involve actually counting the numbers of proteins, but instead measure relative signals, such as fluorescence or absorbance. This implies that they must be calibrated. On the contrary, once the assays performed with the methods and systems herein disclosed that use metal nanoparticles as label compound, has been characterized, there is no need for calibration, since the counting of proteins produces an absolute number that can be correlated to protein concentration.

Figure 19:
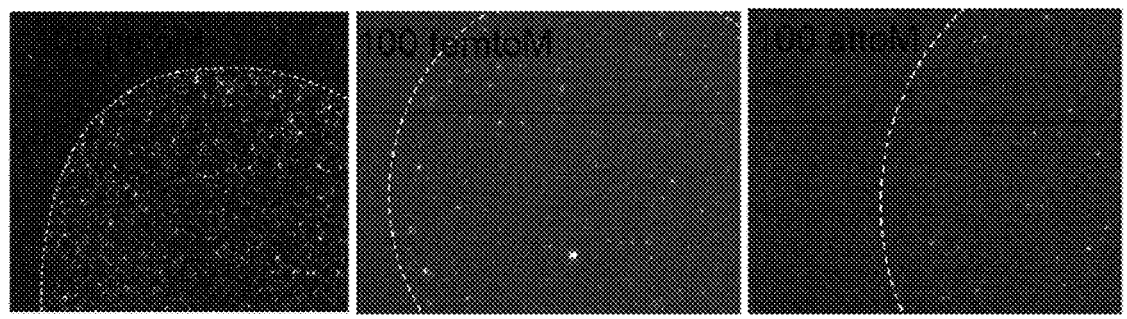
FIG. 19 shows detection of a proteomic with a method and system herein disclosed wherein the detection is performed using Au electroless deposition as a visualization and amplification strategy. Panel a shows detection at concentration of about 100 pM; Panel b shows detection at concentration of about 100 femtoM; Panel c shows detection at concentration of about 100 attoM.
Figure 20:
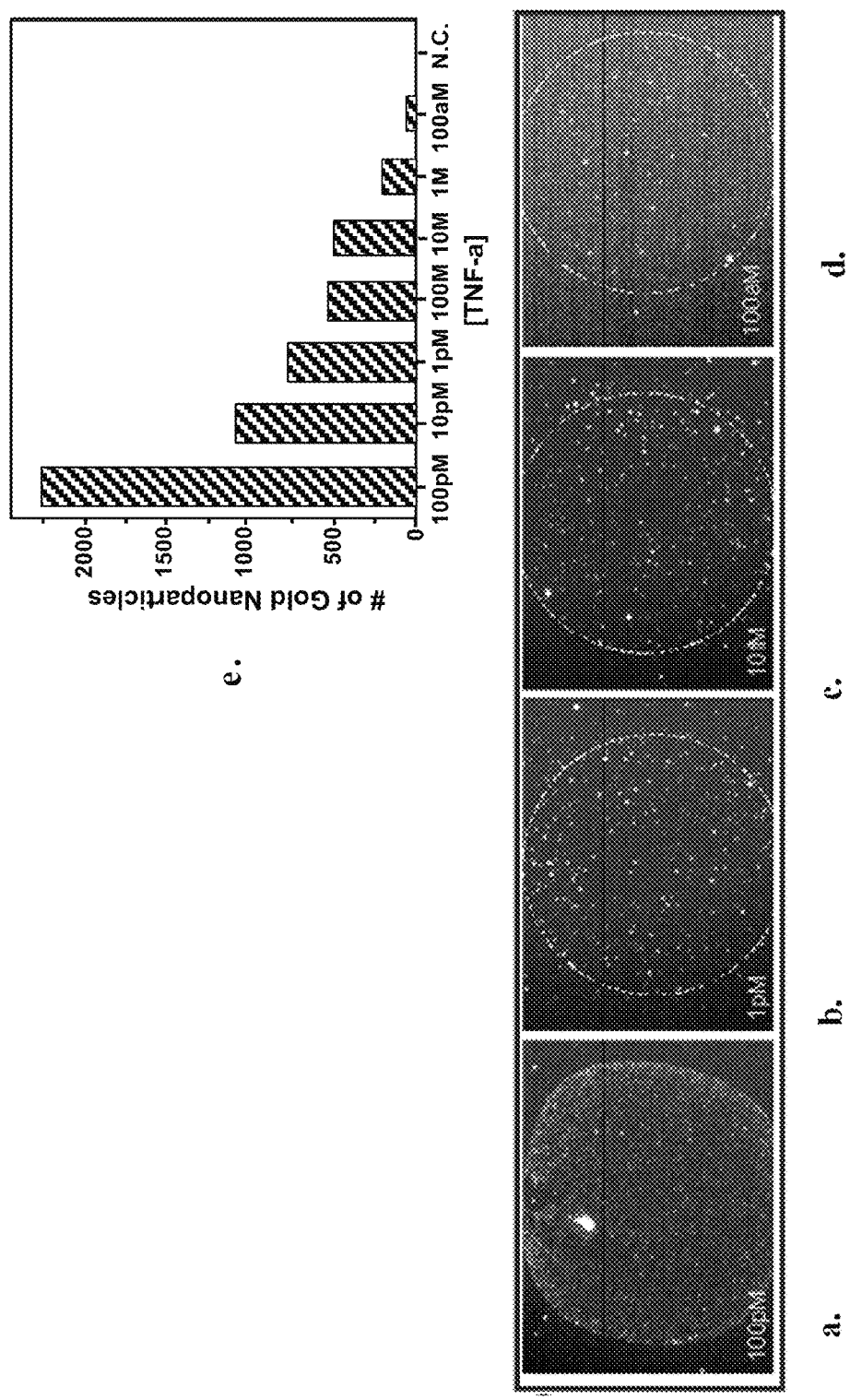
FIG. 20 shows detection of a proteomic with a method and system herein disclosed wherein the detection is performed using Au electroless deposition as a visualization and amplification strategy. Panel a shows detection at concentration of about 100 pM; Panel b shows detection at concentration of about 1 pM; Panel c shows detection at concentration of about 10 fM; Panel d shows detection at concentration of about 100 aM; Panel e shows an histogram correlating the numbers of proteins counted (y axis) versus their concentration in solution (x-axis)

This application would be particularly advantageous for detection the field of proteomics (FIGS. 21 an 22), and/or detection of biomarkers present at a very low concentration in a small volume sample, e.g., a drop of blood (FIGS. 19 and 20).

In additional embodiments, the substrate of any of the methods and systems herein disclosed can be associated with a microfluidic component so to allow performance of microfluidic based assays. Microfluidic-based assays offer advantages such as reduced sample and reagent volumes, and shortened assay times (Breslauer, D. N.; Lee, P. J.; Lee, L. P. *Mol. BioSyst.* 2006, 2, 97-112). For example, under certain operational conditions, the surface binding assay kinetics are primarily determined by the analyte (protein) concentration and the analyte/antigen binding affinity, rather than by diffusion (Zimmermann, M.; Delamarche, E.; Wolf, M.; Hunziker, P. *Biomedical Microdevices* 2005, 7, (2), 99-110).

The term "microfluidic" as used herein refers to a component or system that has microfluidic features e.g. channels and/or chambers that are generally fabricated on the micron or sub-micron scale. For example, the typical channels or chambers have at least one cross-sectional dimension in the range of about 0.1 microns to about 1500 microns, more typically in the range of about 0.2 microns to about 1000 microns, still more typically in the range of about 0.4 microns to about 500 microns. Individual microfluidic features typically hold very small quantities of fluid, e.g from about 10 nanoliters to about 5 milliliters, more typically from about 100 nanoliters to about 2 milliliters, still more typically from about 200 nanoliters to about 500 microliters, or yet more typically from about 500 nanoliters to about 200 microliters.

The microfluidic components can be included in an integrated device. As used herein, "integrated device" refers to a device having two (or more) components physically and operably joined together. The components may be (fully or partially) fabricated separate from each other and joined after their (full or partial) fabrication, or the integrated device may be fabricated including the distinct components in the integrated device. An integrated microfluidic array device includes an array component joined to a microfluidic component, wherein the microfluidic component and the array component are in operable association with each other such that an array substrate of the array component is in fluid communication with a microfluidic feature of the microfluidic component. A microfluidic component is a component that includes a microfluidic feature and is adapted to being in operable association with an array component. An array component is a component that includes a substrate and is adapted to being in operable association with a microfluidic component.

The microfluidic systems can also be provided in a modular form. "Modular" describes a system or device having multiple standardized components for use together, wherein one of multiple different examples of a type of component may be substituted for another of the same type of component to alter the function or capabilities of the system or device; in such a system or device, each of the standardized components being a "module".

Figure 13:
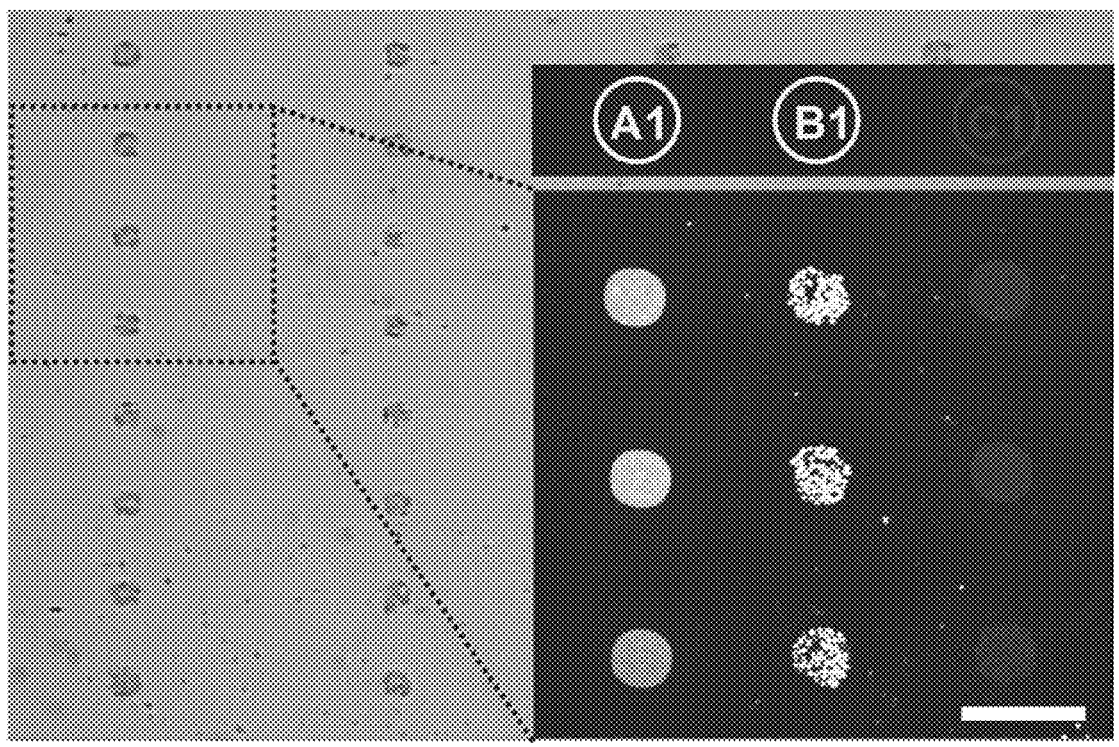
FIG. 13 shows microscopy images demonstrating simultaneous cell capture and multiparameter detection of genes and proteins, the scale bar shown in the Figure corresponding to 300 μm.
Figure 14:
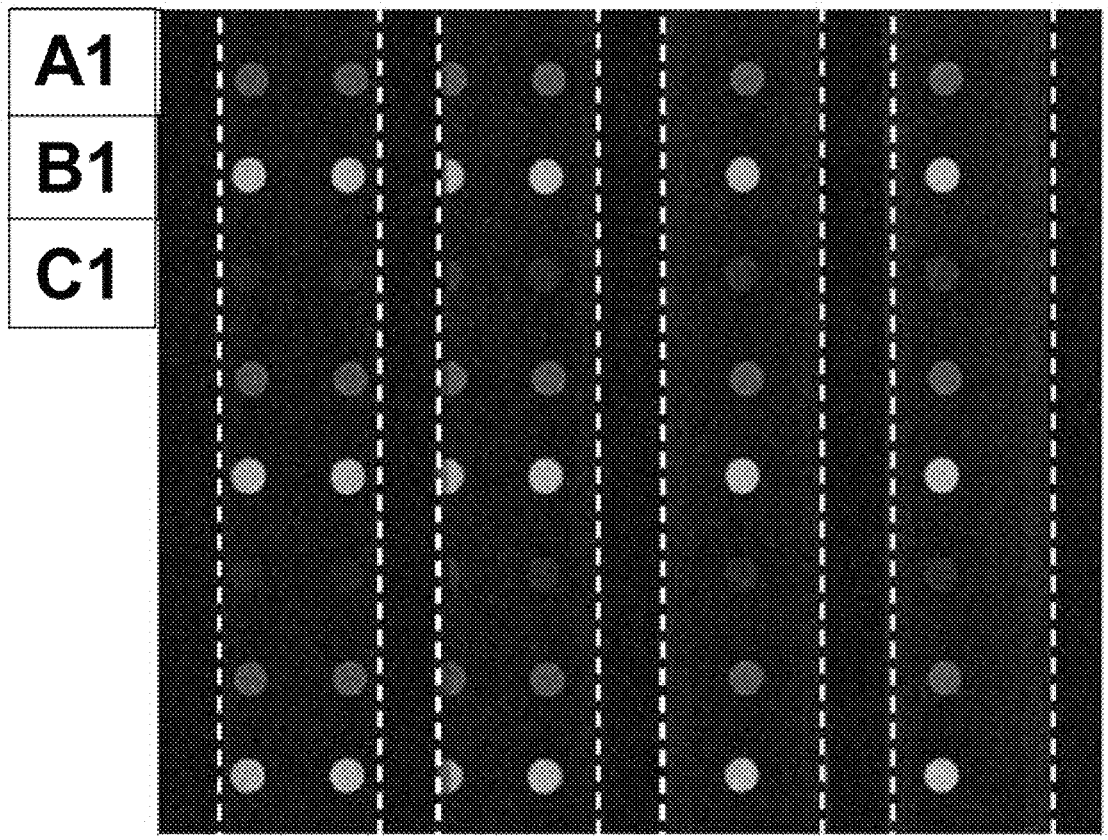
FIG. 14 shows a protein array used in an embodiment of the method for detecting targets herein disclosed assembled in microfluidics.
Figure 15:
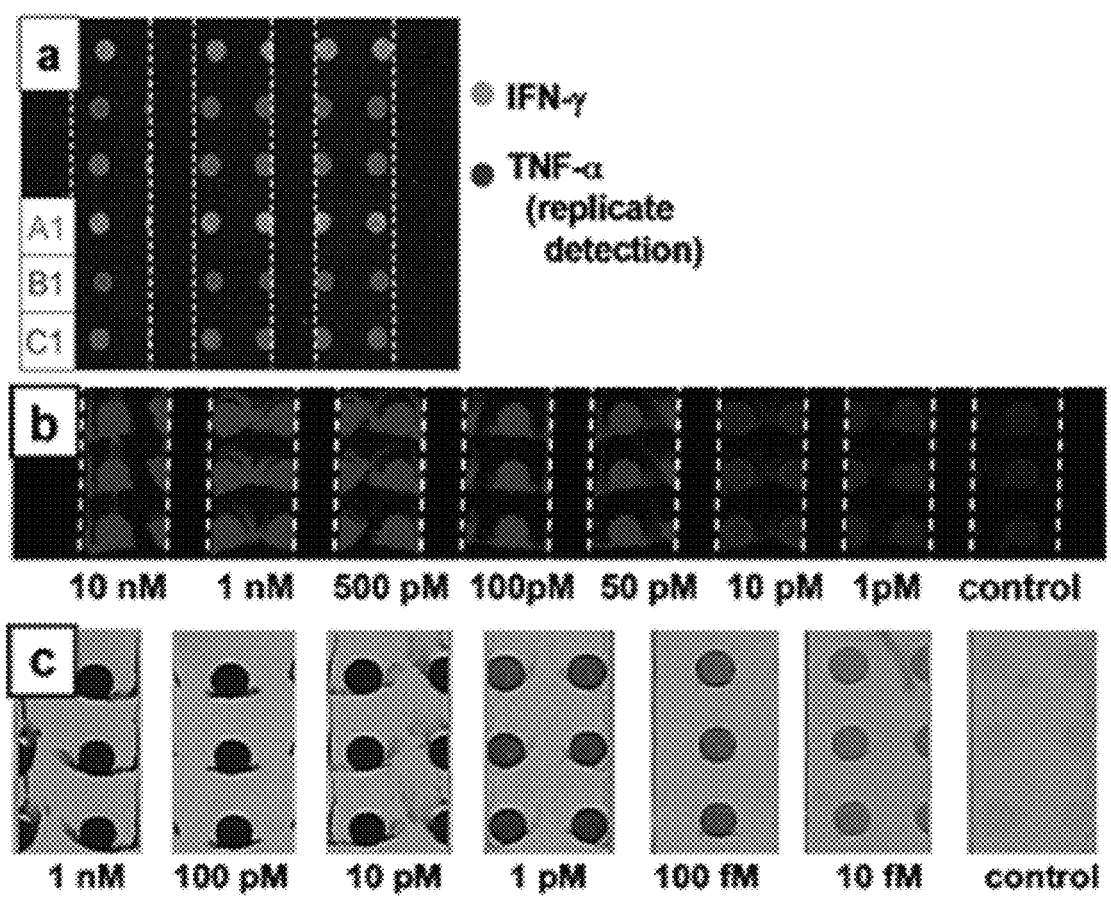
FIG. 15 shows fluorescence and brightfield images of DNA-templated protein immunoassays executed within microfluidic channels, the 600 μm micrometer wide channels being delineated with white dashed lines. Panel a shows a two-parameter immunoassay performed using polynucleotide-encoded antibodies in combination with substrate polynucleotides herein disclosed; Panel b shows detection of a target concentration series in an embodiment of the method and system herein disclosed wherein the detection is performed using fluorescence based techniques; Panel c shows detection of a target concentration series in an embodiment of the method and system herein disclosed wherein the detection is performed using Au electroless deposition as a visualization and amplification strategy.

Exemplary embodiments of the methods and systems herein disclosed to perform microfluidic assays are described in Examples 10 and 11 and illustrated in FIGS. 13 and 14.

In microfluidic embodiments of the methods and systems herein disclosed, measurements of large panels of protein biomarkers within extremely small sample volumes and a very reduced background/biofouling are possible (see FIG. 14).

In the microfluidic embodiments of the methods and systems herein disclosed, the sensitivity of the assay can also be increased to detect targets at a concentration as low as 10 fM, including biomarkers (e.g. proteins in human sera) previously considered below detectable levels by any other techniques.

In the exemplified embodiments, such result is obtained by increasing the loading capacity of the substrate and by using antibodies labeled with metal nanoparticles for the detection, followed by electroless metal deposition (see Example 11 and FIG. 14(*c*)).

Additionally, since in the exemplified embodiments spatial, rather than colorimetric multiplexing, is utilized in the methods and system herein disclosed, a fluorescence based read out can be transformed into an optical one. The microfluidic methods and systems herein disclosed accordingly allow optical read out of assays that are 100-1000 fold more sensitive than corresponding methods and system of the art (see FIG. 14). Accordingly, a further advantage of the microfluidic methods and systems herein disclosed is the possibility of using said methods and systems as a digital technique—i.e. a technique for the quantitative detection of protein via single molecule counting. This application would be particularly advantageous for detection in the field of proteomics (FIG. 14), and/or detection of biomarkers present at a very low concentration in a small volume sample (e.g., a drop of blood)

Additionally, the microfluidic methods and systems herein disclosed allow performance of both (i) mono step assays (wherein the polynucleotide-encoded antibodies the target(s) and labeled antibodies are contacted in a single step) and (ii) multi-steps assays (wherein the substrate is sequentially exposed to polynucleotide-encoded antibodies, target(s), and then secondary antibody) in a reduced amount of time, with samples reduced in size and with a higher sensitivity when compared with corresponding microfluidic methods and system of the art and with other non-microfluidic methods and systems for molecule detection (see Examples 11 and 12).

An additional advantage associated with microfluidic methods and systems herein disclosed includes the possibility of performing in a microfluidic environment any assay that involves substrate-supported antibodies, which would not have survived microfluidic chip assembly with the use of previous techniques.

Further advantages associated with the methods and systems herein disclosed are: the possibility of performing sensitive measurements using low cost reagents, such as glass, and plastic; and of using the substrate in combination with additional components for sample pretreatment and purification The methods and systems herein disclosed allow the multiplexed multiparameter detection, sorting and of biomarkers of interest and related diagnostic analysis. Exemplary illustration of applications of the methods and systems herein disclosed for diagnostic analysis are described in Example 14 and shown in FIGS. 23 and 24, and any additional assay identifiable by a skilled person upon reading of the present disclosure.

The systems herein disclosed can be provided in the form of arrays or kits of parts. An array sometimes referred to as a "microarray" includes any one, two or three dimensional arrangement of addressable regions bearing a particular molecule associated to that region. Usually the characteristic feature size is micrometers. FIGS. 4, 5, 6, 7, 8, 9, and 10 provide exemplary microarrays.

In a kit of parts, the polynucleotide-encoded proteins and a substrate are comprised in the kit independently. The polynucleotide-encoded protein is included in one or more compositions, and each polynucleotide-encoded protein is in a composition together with a suitable vehicle carrier or auxiliary agent.

The substrate provided in the system can have substrate polynucleotide attached thereto. In some embodiments, the substrate polynucleotides can be further provided as an additional component of the kit. Additional components can include labeled polynucleotides, labeled antibodies, labels, microfluidic chip, reference standards, and additional components identifiable by a skilled person upon reading of the present disclosure. In particular, the components of the kit can be provided, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

Further details concerning the identification of the suitable carrier agent or auxiliary agent of the compositions, and generally manufacturing and packaging of the kit, can be identified by the person skilled in the art upon reading of the present disclosure.

EXAMPLES

The methods and system herein disclosed are further illustrated in the following examples, which are provided by way of illustration and are not intended to be limiting.

Example 1

Production of Polynucleotide-Encoded Antibodies

DNA encoded antibodies were generated according to the two step strategy illustrated in FIG. 1. In particular, an aldehyde functionality was introduced to the 5'-aminated oligonucleotide via succinimide chemistry, using commercially available reagents (FIG. 1 Panel a). Similarly, a hydrazide moiety was introduced via reaction with the lysine side chains of the respective antibody (FIG. 1 Panel a). DNA-antibody conjugate formation was then facilitated via stoichiometric hydrazone bond formation between the aldehyde and hydrazide functionalities. Conjugate formation and control over DNA-loading was verified by PAGE electrophoresis (FIG. 1 Panel b).

To perform those experiments, AlexaFluor 488, 594, and 647-labeled polyclonal Goat anti-Human IgGs were purchased from Invitrogen. Monoclonal Rabbit anti-Human Interleukin-4 (clone: 8D4-8), non-fluorescent and APC-labeled Rabbit anti-Human Tumor Necrosis Factor-α (clones: MAb1 and MAb11, respectively), and non-fluorescent and PE-labeled Rabbit anti-Human Interferon-γ (clones: NIB42 and 4S.B3, respectively) were all purchased from eBioscience. Non-fluorescent and biotin-labeled mouse anti-Human Interleukin-2 (clones: 5344.111 and B33-2, respectively) were purchased from BD Biosciences. All DNA strands were purchased with a 5'-amino modification from the Midland Certified Reagent company. Sequences for all six 26-mers and their respective designations are given in Table 1 below together with the respective name/identifier by which the sequences are listed in the enclosed Sequence Listing

TABLE 1

Name/
identifier  Sequence

SEQ ID NO 1 A1: 5'-NH2-AAAAAAAAAACGTGACATCATGCATG-3'

SEQ ID NO 2 3'-GCACTGTAGTACGTACAAAAAAAAAA-NH2-5':
            A1'

SEQ ID NO 3 B1: 5'-NH2-AAAAAAAAAAGGATTCGCATACCAGT-3'

SEQ ID NO 4 3'-CCTAAGCGTATGGTCAAAAAAAAAA-NH2-5':
            B1'

SEQ ID NO 5 C1: 5'-NH2-AAAAAAAAAATGGACGCATTGCACAT-3'

SEQ ID NO 6 3'-ACCTGCGTAACGTGTAAAAAAAAAA-NH2-5':
            C1'

Prior to use, all antibodies were desalted, buffer exchanged to pH 7.4 PBS and concentrated to ~1 mg/ml using 3000 MWCO spin filters (Millipore™).

Hydrazide groups were introduced in parallel onto a monoclonal antibody and 5' aldehyde modified single-stranded DNA was prepared from 5' aminated oligomers (see FIG. 1 Panel a).

In particular, succinimidyl 4-hydrazinonicotinate acetone hydrazone in DMF (SANH, Solulink™) was added to the antibodies at variable molar excess of (1000:1 to 5:1) of SANH to antibody. In this way the number of hydrazide groups introduced to the antibodies was varied. Separately, succinimidyl 4-formylbenzoate in DMF (SFB, Solulink™) was added at a 20-fold molar excess to 5' aminated 26 mer oligomers in PBS. This ratio of SFB to DNA ensured complete reaction of the 5' amine groups to yield 5' aldehydes. No further improvement in yield was observed for both the antibody and oligonucleotide coupling reactions after 4 hours at room temperature. Excess SANH and SFB were removed and samples buffered exchanged to pH 6.0 citrate buffer using protein desalting spin columns (Pierce™).

A 20-fold excess of derivatized DNA was then combined with the antibody and allowed to react overnight at room temperature and form the DNA encoded antibody shown in FIG. 1 Panel b. Non-coupled DNA was removed with size exclusion spin columns (Bio-Gel P-30, Bio-Rad™) or purified using a Pharmacia Superdex 200 gel filtration column at 0.5 ml/min isocratic flow of PBS. The synthesis of DNA-antibody conjugates was verified by non-reducing 7.5% Tris-HCl SDS-PAGE at relaxed denaturing conditions of 60° C. for 5 minutes, and visualized with a Molecular Imager FX gel scanner (Bio-Rad). Conjugation reactions involving fluorescent antibodies or fluorescently-labeled oligonucleotides were imaged similarly using appropriate excitation and emission filters.

Varied oligomer (strand A1') loading unto α-human IL-4 was measured by gel mobility shift assay (see FIG. 1 Panel b). By varying the stoichiometric ratios of SANH to antibody (lanes I-IV corresponds to 300:1, 100:1, 50:1, 25:1 respectively), the average number of attached oligonucleotides can be controlled.

Noticeably, although the above mentioned approach to conjugate synthesis is expected to result in a distribution of DNA loadings for each antibody, this effect might be affected by the methods for performing PAGE analysis. It was in particular observed that normal conditions for the heat-induced denaturation proceeding gel electrophoresis (100° for 5 minutes) reduced the number of DNA-strands visualized, presumably by breaking the hydrazone linkage between the DNA and the protein. By relaxing the denaturing conditions, a sample heated at 60° for 5 minutes (minimum required for good gel) showed up to 7 discrete bands, whereas the same sample heated at 100° for 5 minutes showed no pendant oligonucleotides

Example 2

Production of Polynucleotide-Encoded Streptavidin

The production of DNA encoded streptavidin was performed according to the same approach illustrated in Example 1 for production of DNA encoded antibodies. The only difference was that the SANH:streptavidin ratio was kept constant at 100:1.

Example 3

Optimization Polynucleotides Loading Polynucleotide-Encoded Antibodies

The adverse steric effects of tagging antibodies with oligonucleotides are of concern when performing various assays, such as the immunoassays and cell sorting/capture experiments described herein. For this reason, the ability of DNA-encoded antibodies to retain recognition of cell surface markers, was investigated, as visualized by fluorescence activated cell sorting (FACS). By using a fluorophore covalently-tagged onto the DNA, but not the antibody, FACS was used to optimize DNA-loading for the polynucleotide-encoded conjugates. For the analysis, 5' aminated, 3' FITC-labeled DNA was tagged unto α-CD90.2 antibodies at various stoichiometric ratios of SANH to antibody (5:1, 25:1, 50:1, 100:1, 300:1). This produced, on average, conjugates with 1, 2, 3, 4-5 and 6-7 strands of FITC-DNA respectively, as measured by gel mobility shift assays see Panel d, FIG. 1. These conjugates were tested for their ability to bind to the T cell line VL3 (CD90.2 expressing), by monitoring the FITC fluorescence with the flow cytometer. The B cell line A20 (CD90.2 negative) was used as a negative control (see FIG. 3 Panels a and b).

In particular, VL3 and A-20 cells were incubated for 20 min on ice with 0.5 µg of FITC-conjugated Rat Anti-Mouse CD90.2 (Thy1.2, BD Pharmingen, clone 30-H12, catalog #553012) in 100 µL PBS-3% FCS. Cells were also incubated with equimolar amounts of α-CD90.2/FITC-DNA conjugates characterized by various FITC-DNA loadings. Cells were washed once with PBS-3% FCS and then were analyzed by flow cytometry on a BD FACSCanto™ instrument running the BD FACSDiva™ software.

Figure 3:
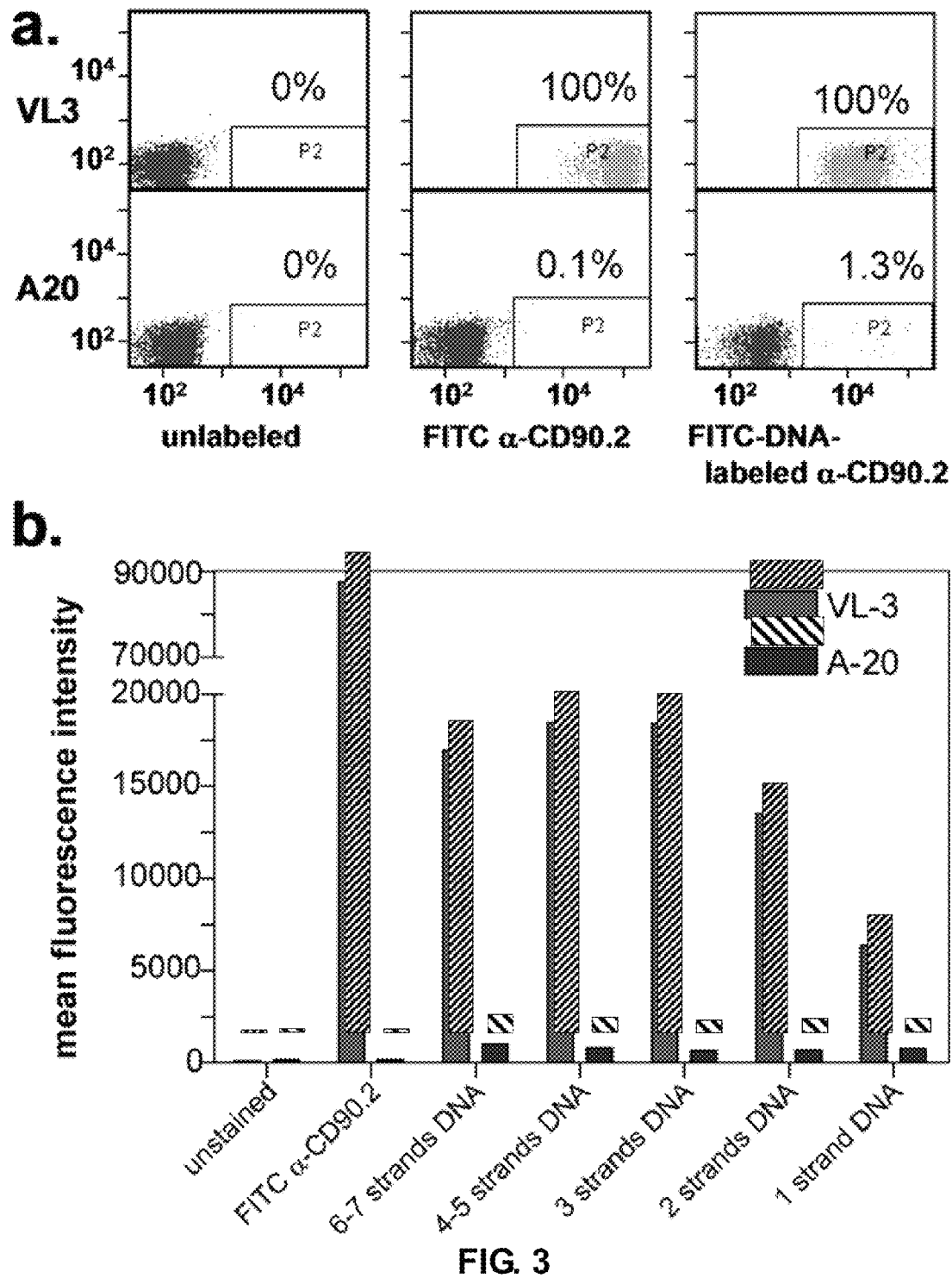
FIG. 3 shows diagrams illustrating the optimization of polynucleotide loading of polynucleotide-encoded antibodies for cell surface marker recognition herein disclosed. Panel a shows FACS plots comparing α-CD90.2/FITC-polynucleotide conjugates (FITC-DNA-labeled α-CD90.2) with FITC α-CD90.2 antibody having no polynucleotide attached to antibody (FITC α-CD90.2) along with a negative control with no antibody and no polynucleotide encoded antibody (unlabeled). The florescent intensity corresponding to the FITC channel is given on the x axis, the y axis corresponding to a null florescent channel; Panel b shows histograms of the mean fluorescent intensities for different numbers of FITC-polynucleotide attached to the antibody; on the x axis the number of polynucleotides attached to the antibody are reported, on the y axis the mean fluorescence intensity is reported.

The results are shown in FIG. 3 where FACS plot (Panel a) and histograms (Panel b) comparing α-CD90.2/FITC-DNA conjugates with the commercially-available FITC α-CD90.2 antibody (no DNA) are shown.

As shown in FIG. 3, the conjugates bind to VL3 cells (100%) with minimal non-specific interactions with A20 (1.3%). When compared with FITC α-CD90.2, the overall fluorescent intensities are lower by a factor of 10, with slightly higher non-specific binding to A20. The histogram of the mean fluorescent intensities for various FITC-DNA loadings illustrated in Panel b shows that the fluorescence increases are roughly linear when the number of DNA strands is increased from 1 to 2 to 3, corresponding to the 1, 2 and 3 chromophores (1 per strand). For higher loadings, the fluorescence plateaus and then decreases.

In particular, at higher loadings, the increase in fluorescence first plateaus (4-5 oligomers) and then decreases up to the highest loading (6-7 oligomers). Thus, excess DNA labels (4-7 oligomers) did sterically reduce the ability of antibodies to recognize cell surface markers. Optimal loading for cell surface marker recognition was achieved with antibodies synthesized with the 50:1 SANH:antibody ratio—corresponding to approximately three DNA strands per antibody. Subsequent cell sorting experiments were performed in consideration of this observation. When compared with the FITC α-CD90.2 control, the DNA antibody conjugates had reduced fluorescence by a factor of 10 and slightly higher nonspecific binding to A20 cells. A likely factor is that the stoichiometric ratio of fluorophore to antibody for the DNA antibody conjugates versus the commercial antibody is different. For the DNA antibody conjugates, each strand of DNA is attached to one fluorophore only (i.e. conjugates with one DNA strand has a fluorophore to antibody ratio of 1:1) whereas the commercial antibodies generally have more than one fluorophore per antibody (i.e. fluorescent antibodies have a fluorophore to antibody ratio >1).

Thus the factor of 10 less fluorescence should not be strictly interpreted as a 10× reduction in the binding affinity of the DNA antibody conjugates, although it is possible that the oligomer steric effects discussed earlier do account for some reduction in relative fluorescence intensity. Direct measurement of the affinity of the DNA antibody conjugate compared with the corresponding unmodified antibody using methods like Surface Plasmon Resonance (SPR) can provide more conclusive information.

A further optimization of polynucleotides loading of the polynucleotide-encoded-antibodies was performed as follows. Two different lengths of complementary polynucleotides were invested. One set had an overlap of 16 bases, the other an overlap of 20 bases. Orthogonal DNA sequences for set of 16 or 20 were designed according to procedures exemplified in Example 8 below, and it was discovered empirically that 16 bases did not have the variability in the total number of sequences possible to generate large numbers of orthogonal sequences. In moving to 20 bases, the initial pool of possible sequences dramatically increased and computing orthogonal sequences seemed to be much easier. It should be noted that the total number of possible sequences is exponential ($4^n$, where n is the length of the complementary region).

Example 4

Microarray Fabrication

DNA microarrays were printed via standard methods by the microarray facility at the Institute for Systems Biology (ISB—Seattle, Wash.) onto amine-coated glass slides. In particular, the DNA microarrays were printed with various combination of oligomers having sequences SEQ ID NO 2, SEQ ID NO 4, SEQ ID NO 6, SEQ ID NO 8, SEQ ID NO 10, SEQ ID NO 12, SEQ ID NO 14, SEQ ID NO 16, and SEQ ID NO 18, Typical spot size and spacing were 150 and 500 μm, respectively. Poly-lysine slides were made in house. Blank glass slides were cleaned with IPA and water in a sonication bath for 10 minutes each. They were then treated with oxygen plasma at 150 W for 60 sec., and then quickly dipped into DI water to produce a silanol terminated, highly hydrophilic surface. After drying them with a nitrogen gun, poly-L-lysine solution (Sigma P8920, 0.1% w/v, without dilution) was applied to the plasma treated surfaces for 15 minutes, and then rinsed off with DI water for several seconds. Finally, these treated slides were baked at 60° C. for 1 hr. These slides were then sent to ISB and printed as described above.

Example 5

Monoparameter Polynucleotide-Encoded Antibody-Based Immunoassays

FIG. 5 is an example of using DNA-encoded streptavidin to perform cell sorting experiments. Here the DNA-encoded streptavidin is first exposed to its ligand, biotin labeled protein at a ratio of 4:1 biotin-MHC: DNA-encoded streptavidin. Here the protein is the major histocompatiblity complex (MHC). Both the panning analog and solution phase cell capture experiments are performed in parallel. In particular, 5 ul of Streptavidin-C3' is combined with 20 ul of tyrosinase MHC in 200 ul of RPMI media. They are allowed to assemble on ice for 20 min. After which, for the panning analog, the tetramer is allowed to bind to the substrate for 30 minutes and rinsed in PBS before subsequence exposure of $2 \times 10^6$ cells onto the array. In Panel b, DNA-encoded MHC is first allowed to bind to the same number of cells on ice for 20 min. before subsequent exposure to the underlying DNA array. The cell capture efficiencies between the two panels are apparent. Solution phase capture for pMHC complexes is much higher than the panning analog. Of notice is the enhanced cell capture efficiency of the latter series of events.

Example 6

Protein Arrays Including Polynucleotide-Encoded Antibody

The polynucleotide-encoded protein approach for spatially localizing antibodies was demonstrated using three identical goat anti-human IgGs, each bearing a different molecular fluorophore and each encoded with a unique DNA strand. A solution containing all three antibodies was then introduced onto a microarray spotted with complementary oligonucleotides. After a two-hour hybridization period and substrate rinse, the antibodies self-assembled according to Watson-Crick base-pairing.

In particular, antibody microarrays were generated by first blocking the DNA slide with 0.1% BSA in 3×SSC for 30 minutes at 37° C. The slides were washed with $dH_2O$ and blown dry. A 30 μl solution containing DNA-antibody conjugates (3×SSC, 0.1% SDS, 0.1% BSA, 15 ng/μl of each conjugate) was sandwiched to the array with a microscope slide, and incubated at 37° C. for 4 hours. Arrays were then washed first in 1×SSC, 0.05% SDS at 37° C. with gentle agitation, then at 0.2×SSC, then finally at 0.05×SSC. The slides were blown dry and scanned with a Gene Pix 4200 A two-color array scanner (Axon Instruments™).

For the immunoassays, the DNA-encoded 1° antibody (15 ng/μl), antigen (3 ng/μl) and fluorescently-labeled 2° antibody (0.5 ng/μl) were combined in a single tube. After 2 hour incubation at 37° C., the formed antibody-antigen-antibody complexes were introduced to the microarrays as described above in Example 3. Subsequent wash steps and visualization were identical In particular, three biochemically identical goat α-human IgG (labeled with Alexa488, Alexa594, or Alexa 647 dyes) were tagged with oligos A1', B1' and C1' respectively. After a 2-hour incubation, antibody/DNA conjugates were localized to specific sites dictated by the underlying DNA microarray.

Figure 7:
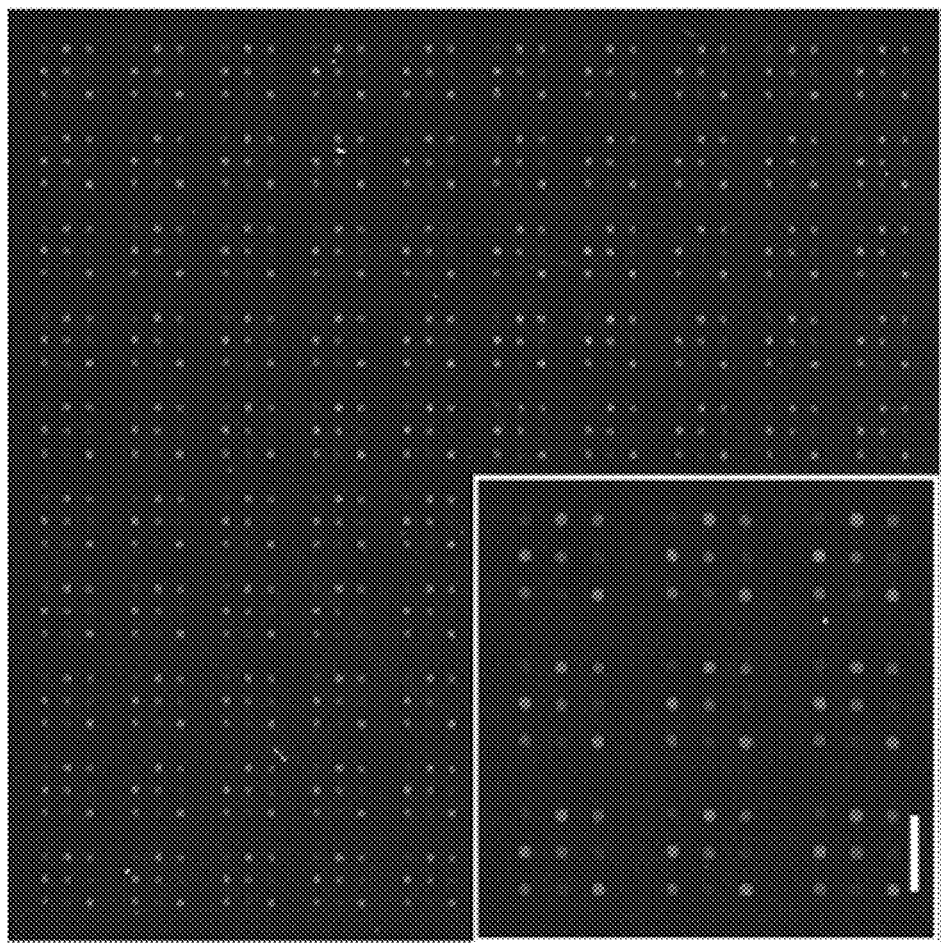
FIG. 7 shows a spatially encoded protein array using encoded polynucleotide-encoded antibodies and substrate polynucleotides herein disclosed. Panel a shows an immunoassay performed with three identical goat α-human IgG (labeled with Alexa488, Alexa594, or Alexa 647 dyes) and tagged with polynucleotides A1', B1' and C1' respectively; shows a schematic representation of the results of the immunoassays from the portion of the array of Panel a indicated by a white bar; the scale bar shown in the Figure corresponding to 1 mm.

The results are shown in FIGS. 6 and 7, wherein a spatially encoded-protein array with a scale bar that corresponds to 1 mm is shown. As it is evident from FIG. 7, the antibodies assemble with the DNA on the substrate thus converting the >900 spot complementary DNA chip into a multi-element antibody microarray (see FIG. 7). This observation implied that quite large antibody arrays can be assembled in similar fashion.

Example 7

Reduction of Biofouling

The ultimate size of any protein array is likely be limited by interference from non-specific binding of proteins. In an effort to visualize the contributions of non-specific binding, three antibodies were similarly introduced onto a microarray: two antibodies having complementary DNA-labeling spotted oligonucleotides and a third unmodified antibody. In particular, a microarray was simultaneously exposed to goat α-human IgG-Alexa488/A1', goat α-human IgG-Alexa647/C1' polynucleotide-encoded conjugates and goat α-human IgG-Alexa594 with no pendant DNA.

For demonstration purposes, the slide was not thoroughly rinsed following hybridization and accordingly a high background signal due to non-specific adsorption of non-encoded fluorescently-labeled antibody was observed.

Figure 8:
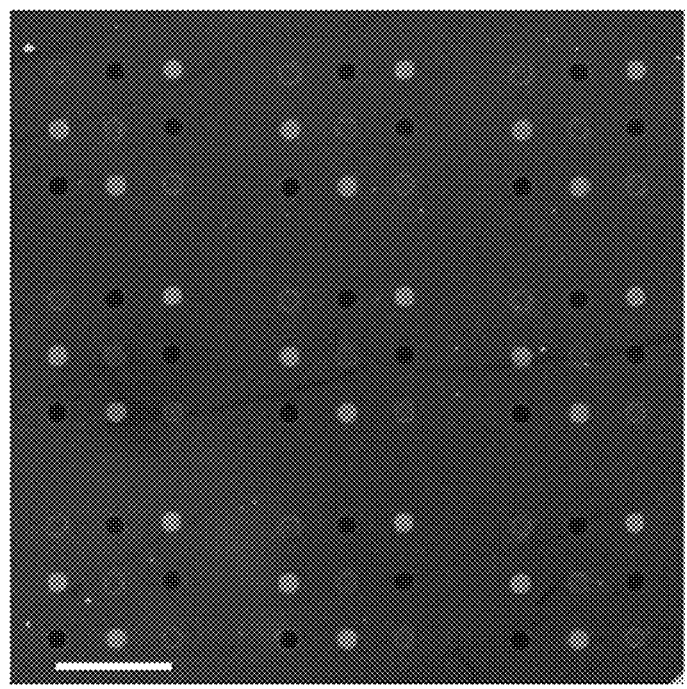
FIG. 8 shows the results of an immunoassay showing minimization of non specific protein absorption resulting from the combined used of polynucleotide-encoded antibodies and substrate polynucleotide herein disclosed. Panel a shows a microarray simultaneously exposed to goat α-human IgG-Alexa488/A1', goat α-human IgG-Alexa647/C1' each conjugated with a specific polynucleotide and goat α-human IgG-Alexa594 with no pendant DNA, Panel b shows a schematic representation of the results of the immunoassays from the portion of the array of Panel a indicated by a white bar; the scale bar shown in the Figure corresponding to 1 mm.

The results are shown in FIG. 8 that is an illustration of the resistance of the polynucleotide encoded-protein approach towards non-specific protein absorption.

When the arrays were not fully blocked and/or rinsed, non-specific binding was observed on the surface of the glass slide, but not on the non-complementary spots of printed DNA, i.e., spot B1 did not have fluorescence from non-complementary IgG conjugates nor did it exhibit fluorescence from proteins not encoded with DNA (goat α-human IgG-Alexa594).

The spotted nucleotide regions, to which no antibody was chemically encoded, displayed much less non-specifically attached protein, implying that DNA greatly diminishes active area biofouling. Such retardation of biofouling is reminiscent of substrates that are functionalized with polyethyleneglycol (PEG) (Prime, K. L.; Whitesides, G. M. *Science* 1991, 252, 1164-1167. Prime, K. L.; Whitesides, G. M. *J. Am. Chem. Soc.* 1993, 115, (23), 10714-10721). By analogy with postulated mechanisms associated with PEG (Jeon, S. I.; Lee, J. H.; Andrade, J. D.; De Gennes, P. G. *Journal of Colloid and Interface Science* 1991, 142, (1), 149-158. Jeon, S. I.; Andrade, J. D. *Journal of Colloid and Interface Science* 1991, 142, (1), 159-166. Andrade, J. D.; Hlady, V. *Advances in Polymer Science* 1986, 79, (1-63)), the Applicants hypothesize that the hydrophilic nature of the spotted oligonucleotides minimizes interactions with hydrophobic portions of proteins often exposed during non-specific adsorption. Conjugate hybridization experiments were also carried out within 5 degrees of the calculated duplex melting temperatures, taking advantage of Watson-Crick stringencies and thus diminishing non-complementary DNA interactions. In any case, this reduced biofouling means that the polynucleotide-encoded-protein method can likely be harnessed to detect reasonably large panels of proteins within a single environment.

Example 8

In Silico Polynucleotide Orthogonalization

Another important empirical observation is the level of cross talk between non-complementary DNA strands. The DNA sequences A1, B1, C1 along with their complements were generated randomly. The inclusion of a 5' $A_{10}$ segment for flexibility and a recognition length of 16 bases were the only constraints. In running the experiments, it was discovered that there is a low but appreciable amount of noise generated from mismatched sequences due to non-linear secondary interactions. Stringency washes alone were not able to clean the noise appreciably. In any realistic multiparameter platform, this noise can grow in proportion to the number of parameters in investigation. Thus, the model platform should utilize DNA sequences which are orthogonal to each other and also orthogonal to all the exposed complementary strands printed on the DNA array.

As a consequence, DNA sequences were designed with the objective of minimizing any intra- and intermolecular interactions between the sequences and the complementary targets, at 37° C. The computational design was performed using the paradigm outlined by Dirks et al. (Dirks, R. M.; Lin, M.; Winfree, E.; Pierce, N. A. *Nucleic Acids Research* 2004, 32, (4), 1392-1403). In particular, six orthogonal sequences have been designed and empirically verified and are reported in Table 2.

TABLE 2

| Encoding-polynucleotide | Corresponding substrate polynucleotide |
|---|---|
| SEQ ID NO: 7 AAAAAAAAAAATCCTGGAGCTAAGTCCGTA | SEQ ID NO: 8 AAAAAAAAAATACGGACTTAGCTCCAGGAT |
| SEQ ID NO: 9 AAAAAAAAAAGCCTCATTGAATCATGCCTA | SEQ ID NO: 10 AAAAAAAAAATAGGCATGATTCAATGAGGC |
| SEQ ID NO: 11 AAAAAAAAAAAGCACTCGTCTACTATCGCTA | SEQ ID NO: 12 AAAAAAAAAATAGCGATAGTAGACGAGTGC |
| SEQ ID NO: 13 AAAAAAAAAAATGGTCGAGATGTCAGAGTA | SEQ ID NO: 14 AAAAAAAAAATACTCTGACATCTCGACCAT |
| SEQ ID NO: 15 AAAAAAAAAAATGTGAAGTGGCAGTATCTA | SEQ ID NO: 16 AAAAAAAAAATAGATACTGCCACTTCACAT |
| SEQ ID NO: 17 AAAAAAAAAAATCAGGTAAGGTTCACGGTA | SEQ ID NO: 18 AAAAAAAAAATTACCGTGAACCTTACCTGAT |

A skilled person can identify additional orthogonalized polynucleotides upon reading of the present disclosure.

Example 9

Cell Capture, Separation, and Sorting Methods

The optimization and use of the polynucleotide-encoded-protein for multiplexed cell sorting was demonstrated by using DNA labeled antibody.

Two murine cell lines, VL-3 T cells (thymic lymphoma line (Groves, T.; Katis, P.; Madden, Z.; Manickam, K.; Ramsden, D.; Wu, G.; Guidos, C. J. *J. Immunol.* 1995, 154, 5011-5022)) and A20 B cells (mouse B cell lymphoma (Kim, K. J.; Langevin, C. K.; Merwin, R. M.; Sachs, D. H.; Asfsky, R. *J. Immunol.* 1979, 122, 549-554), purchased from ATCC) were engineered to express mRFP and EGFP, respectively, using standard retroviral transduction protocols. Antibodies against surface markers for each of these cell lines, α-CD90.2 for VL-3 and α-B220 for A20 (eBioscience), were encoded as described above with DNA strands A1' and B1', respectively.

For sorting experiments, cells were passaged to fresh culture media [RPMI 1640 (ATCC) supplemented with 10% fetal bovine serum, 0.1 mM non-essential amino acids and 0.05 mM β-mercaptoethanol] at a concentration of $10^6$ cells/ 100 μl media and incubated with DNA-antibody conjugate (0.5 μg/100 μl) for 30 minutes on ice. Excess conjugate was removed from the supernatant after centrifugation, after which cells were resuspended in fresh media. Prior to cell incubation the microarray slide was passivated, to reduce non-specific cell adhesion, by reaction of the residual amine groups with methyl-$PEO_{12}$—NHS ester (Pierce) 10 mM in pH=7.4 PBS for 4 hours at room temperature. Cells were spread evenly across the microarray surface and allowed to localize for one hour on ice. After this period, non-adherent cells were removed with gentle washing with room temperature Tris-buffered saline solution including 1 mM $MgCl_2$. Cell enrichment experiments were performed identically except that all incubation steps were performed in the presence of a 1:1 mixture of both T- and B-cells (each at $10^6$/100 μl).

Primary CD4+ and CD8+ T cells were purified from EGFP and dsRed transgenic mice (obtained from Jackson Laboratories), respectively, using standard magnetic bead negative selection protocols and the BD IMag™ cell separation system. Prior to polynucleotide-encoded based fractionation, the purity of these populations was analyzed by FACS and found to be greater than 80%.

Simultaneous cell, gene and protein experiments were performed similarly to those as previously described on a PEGylated microarray substrate.

Briefly, GFP-expressing B cells ($10^6$/100 μl) were located on B1 spots after labeling with α-B220-B1' (0.5 μg/100 μl). Following removal of non-adherent cells, a TNF-α ELISA pair with C1'-encoded 1° and APC-labeled 2° antibodies were introduced along with 0.5 ng/μl FITC-labeled A1' and allowed to hybridize for a period of 30 minutes at room temperature. The slide was then rinsed with TBS+$MgCl_2$ and visualized via brightfield and fluorescence microscopy.

Homogeneous and panning cell experiments were performed in parallel. For the homogenous cell capture process, $5×10^6$ Jurkats (ATCC) suspended in 1 ml of RPMI media along with 5 μg of α-CD3/C3' conjugates and incubated on ice for 1 hour. Excess conjugates were removed by centrifugation and the Jurkats were resuspended into 200 μl of fresh media before exposure to the DNA microarray. After 1 hour incubation on ice, the slides were rinsed gently with TBS. The cell panning experiments were performed in parallel; 5 μg of α-CD3/C3' conjugate in 1 ml RPMI media was incubated on a microarray for 1 hour on ice before rinsing in 0.5×PBS, then deionized water. The slide was not blown dry, but gently tapped on the side to remove the majority of the excess solution, keeping the array hydrated. Jurkats ($5×10^6$/200 μL) were immediately placed on the array for one hour on ice. Subsequent wash and visualization steps are identical.

Figure 10:
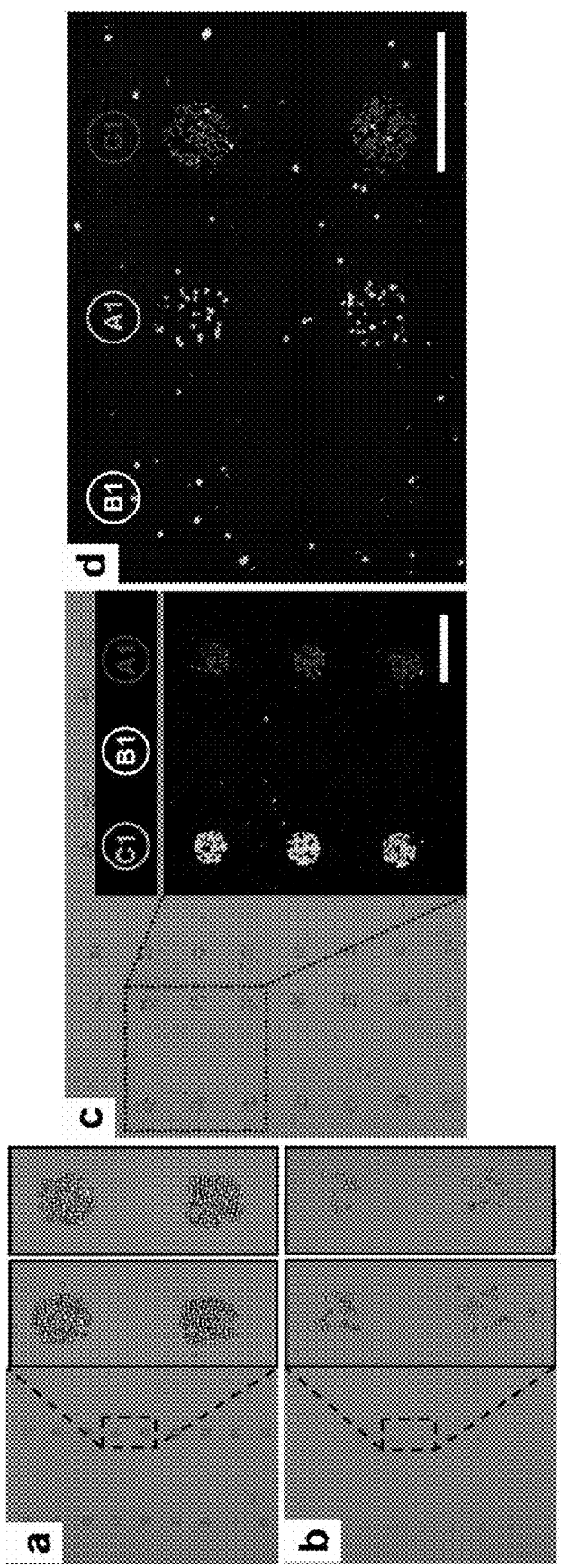
FIG. 10 illustrates a method for performing multiplexed cell sorting. using the polynucleotide-encoded antibody and the substrate polynucleotide herein disclosed. Panel a. shows a homogeneous assay in which polynucleotide-encoded antibodies are combined with the cells, and then the mixture is introduced onto the spotted DNA array microchip; Panel b shows polynucleotide-encoded antibodies assembled onto a spotted DNA array, followed by introduction of the cells; Panel c shows brightfield and fluorescence microscopy images of multiplexed cell sorting experiments where a 1:1 mixture of mRFP-expressing T cells (red channel) and EGFP-expressing B cells (green channel) is spatially stratified onto spots A1 and C1, corresponding to the encoding of α-CD90.2 and α-B220 antibodies with A1' and C1', respectively; Panel d. is a fluorescence micrograph of multiplexed sorting of primary cells harvested from mice. A 1:1 mixture of CD4+ cells from EGFP transgenic mice and CD8+ cells from dsRed transgenic mice are separated to spots A1 and C1 by utilizing polynucleotide-encoded conjugates α-CD4-A1' and αCD8-C1', respectively.

The results of these experiments are illustrated in FIG. 10 wherein Panels a and b show brightfield images showing the efficiency of the homogeneous cell capture process according to an embodiment of the methods and systems herein disclosed.

In particular, in Panel a, a homogeneous assay is described in which DNA labeled antibodies are combined with the cells, and then the mixture is introduced onto the spotted DNA array microchip. In Panel b, DNA labeled antibodies are first assembled onto a spotted DNA array, followed by introduction of the cells. This heterogeneous process is similar to the traditional panning method of using surface bound antibodies to trap specific cells.

By comparing the results illustrated in Panels a and b, the polynucleotide-encoded protein based cell sorting was compared with panning by evaluating homogeneous cell capture (solution phase cell capture) and heterogeneous capture of cells (surface confined cell capture). The homogeneous DNA-encoded protein method exhibited a higher cell capture efficiency.

The increase in capture efficiency can be attributed to several factors. In homogeneous cell capture, the DNA-antibody conjugates are allowed to properly orient and bind to the cell surface markers in solution. Cell capture is not driven by antibody to cell surface marker interactions, but rather by the increased avidity of the multivalent DNA-antibody conjugates for the complementary DNA strands on the microarray through cooperative binding, greatly increasing capture efficiency. Similar trends have been reported for nanoparticle, DNA hybridization schemes (Taton, T. A.; Mirkin, C. A.; Letsinger, R. L. *Science* 2000, 289, 1757-1760). With panning methods, which are analogous to a heterogeneous DNA-antibody defined arrays herein disclosed, the capture agents are restricted to adopt a random orientation on the surface. The activity of the antibodies is reduced, simply because of improper orientation for interaction with the cell surface markers, decreasing maximum avidity and cooperation with neighboring antibodies.

In Panel c, brightfield and fluorescence microscopy images of multiplexed cell sorting experiments are shown, where a 1:1 mixture of mRFP-expressing T cells (red channel) and EGFP-expressing B cells (green channel) is spatially stratified onto spots A1 and C1, corresponding to the encoding of α-CD90.2 and α-B220 antibodies with A1' and C1', respectively. In particular, in the experiments of FIG. 10c, two unique DNA strands were conjugated to antibodies raised against the T cell marker CD90.2 (Thy1.2) and the B cell marker CD45R (B220), respectively. Multiplexed DNA-antibody-based cell sorting was demonstrated by spatially separating a 1:1 mixture of monomeric Red fluorescent protein (Campbell, R. E.; Tour, O.; Palmer, A. E.; Steinbach, P. A.; Baird, G. S.; Zacharias, D. A.; Tsien, R. Y. *Proc. Natl. Acad. Sci.* 2002, 99, 7877-7882) (mRFP)-expressing T cells (VL-3, murine thymic lymphoma) and EGFP-expressing B cells (mouse B cell lymphoma). This mixture was incubated with uniquely-encoded DNA-antibody conjugates against both T and B cell markers and introduced to an appropriately spotted microarray. The results show both brightfield and false color fluorescence micrographs demonstrating that the mRFP-expressing T cells are enriched at spots A1 and EGFP-expressing B-cells located at B1, consistent with the DNA-encoding of the respective antibodies.

In Panel d, a fluorescence micrograph of multiplexed sorting of primary cells harvested from mice. A 1:1 mixture of CD4+ cells from EGFP transgenic mice and CD8+ cells from dsRed transgenic mice is separated to spots A1 and C1 by utilizing polynucleotide-encoded conjugates α-CD4-A1' and α-CD8-C1', respectively. Primary cells are usually more fragile than established cell lines. This is due to the fact that they have to be extracted (usually by enzymatic digestions) from the surrounding tissues, a process that can lead to decreased viability. Moreover, the culture process often selects for clones characterized by greatly increased viability as well as proliferation potential. A generalized cell sorting technology must therefore also work on primary cells with minimal sample manipulation. To demonstrate the utility of the polynucleotide-encoded-protein approach for primary cell sorting, a synthetic mixture of CD4+ and CD8+ T cells was isolated via magnetic negative depletion from EGFP- and dsRED-transgenic mice, respectively. The mixture was stratified using α-CD4 and α-CD8 DNA-antibody conjugates. As shown in FIG. 10d, the two cell types were separated to different spatial locations according to the pendant DNA encoding.

Example 10

Figure 12:
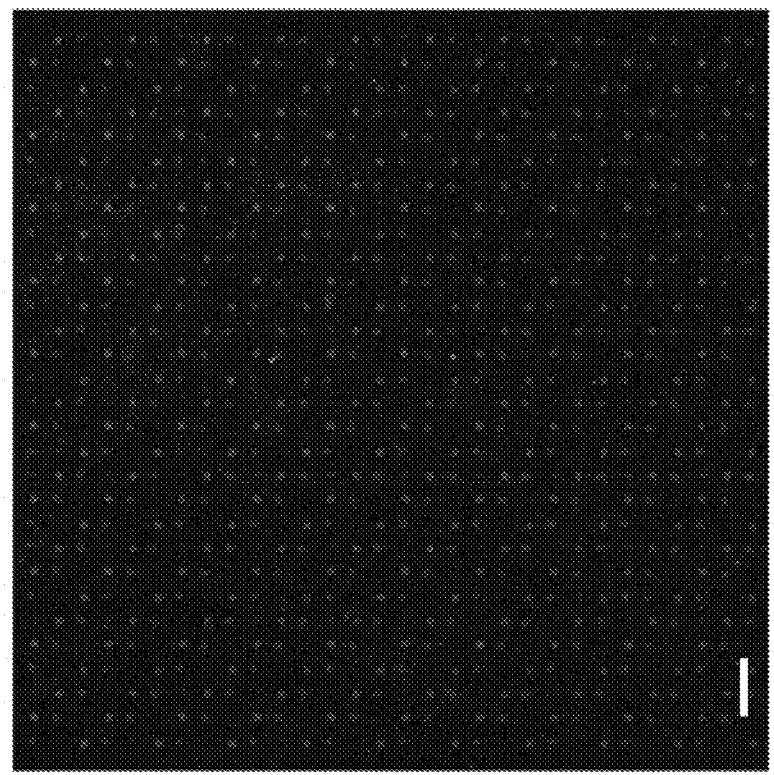
FIG. 12 illustrates the ability of a polynucleotide-encoded protein to detect a plurality of targets according to an embodiments of the methods and systems herein disclosed; Panel a, shows a microarrays exposed to an antibody specific for antigen IL4 encoded with polynucleotide C1 and a polynucleotide complementary to polynucleotide B1 labeled with a fluorophore; Panel b shows a schematic representation of the embodiment of the methods and systems herein disclosed used to perform the assay; Panel c shows a schematic representation of the results of the assay illustrated in the portion of panel A identified by a white bar.
Figure 12:
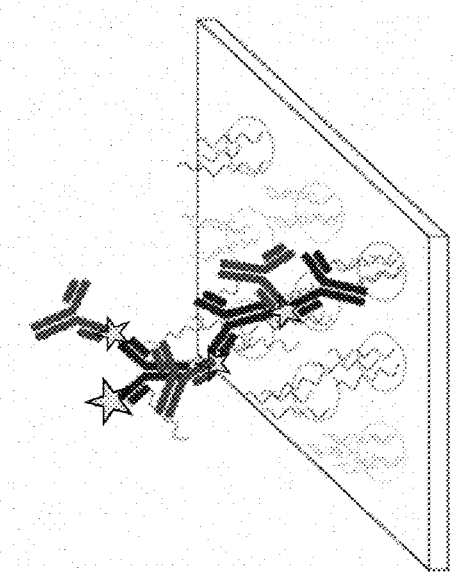
Figure 12:
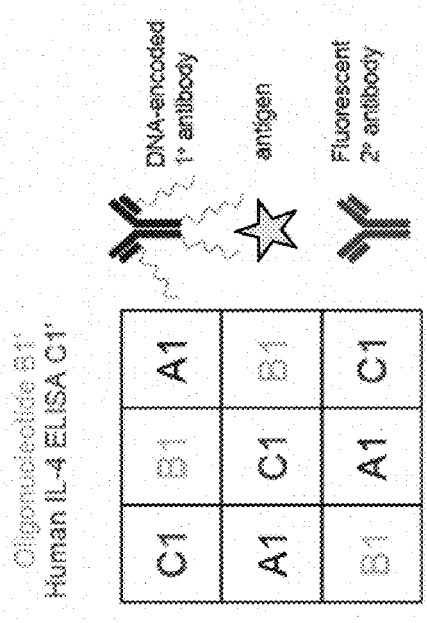

Multiparameter Multiplexed Analysis Using DNA Encoded Antibodies in Combination with DNA Printed Array A multiparameter analysis (cells, mRNAs and proteins) was performed according to the strategy schematically described in FIG. 12.

FIG. 11 is an illustration of the polynucleotide-encoded protein method for cell sorting and co-detection of proteins and cDNAs (mRNAs). Antibodies against proteins (for cell sorting) or other proteins (including cell surface markers) are labeled with distinct DNA oligomers. These conjugates may then be combined with the biological sample (cells, tissue, etc.) where they bind to their cognate antigens. When introduced onto a DNA microarray, parallel self assembly, according to Watson-Crick base pairing, localizes the bound species to a specific spatial location allowing for multiplexed, multi-parameter analysis.

An immunoassay was performed to illustrate the ability of polynucleotide-encoded protein herein disclosed to detect a plurality of targets, including chemically different targets. In particular, the assay was performed for the detection of protein target IL4 and a polynucleotide B1. To this purpose, an antibody specific to the protein target IL4 was encoded with polynucleotide C1 and a polynucleotide complementary to polynucleotide B1 was prepared. The polynucleotide complementary to polynucleotide B1 was incubated together with the C1' encoded anti-IL4 as described above. Upon specific binding, a fluorophore secondary antibody to IL4 was introduced, and the simultaneous detection of the protein target IL4, and the oligonucleotide B1 performed as illustrated in FIG. 12.

To highlight the universal diversity of the platform schematically illustrated in FIG. 11, GFP-expressing B cells were tagged with BF DNA-encoded antibody conjugates and spatially located onto spots (B1) encoded with the complementary oligonucleotide. Post cell localization, FITC-labeled A1' DNA and a C1'-encoded TNF-α immunosandwich, were combined and introduced to the same microarray platform. The resulting brightfield and fluorescence microscopy images, shown in FIG. 13, demonstrate the validity of a platform according to an embodiment of the methods and systems herein disclosed, for simultaneously extending across different levels of biological complexity.

In particular, FIG. 13 shows microscopy images demonstrating simultaneous cell capture at spot B1 and multiparameter detection of genes and proteins, at spots A1 and C1, respectively. The brightfield image shows EGFP-expressing B cells (green channel) located to spots B1, FITC-labeled (green) cDNA at A1, and an APC-labeled TNF-α sandwich immunoassay (blue) encoded to C1. The scale bar corresponds to 300 µm.

The efficiency of the polynucleotide-encoded-protein methods and systems exemplified herein can possibly be ascribed to the use of polynucleotide specific binding to anchor the antibody to the substrate. Conventional antibody arrays for protein detection or for panning cells (Wysocki, L. J.; Sato, V. L., *Proc. Natl. Acad. Sci.* 1978, 75, (6), 2844-2848) require immobilization of the antibody on to aldehyde, epoxy, maleimide, or hydrophobic solid supports (Liu, X.; Wang, H.; Herron, J.; Prestwich, G., *Bioconjugate Chem.* 2000, 11, (755-761). Macbeath, G.; Schreiber, S. L. *Science* 2000, 289, 1760-1763. Pal, M.; Moffa, A.; Sreekumar, A.; Ethier, S.; Barder, T.; Chinnaiyan, A.; Lubman, D. *Anal. Chem.* 2006, 78, 702-710. Thirumalapura, N. R.; Morton, R. J.; Ramachandran, A.; Malayer, J. R. *Journal of Immunological Methods* 2005, 298, 73-81). It is often difficult to preserve folded (active) antibody conformations due to surface induced denaturation which depends on many variables including pH, ionic strength, temperature and concentration (Seigel, R. R.; Harder, P.; Dahint, R.; Grunze, M.; Josse, F.; Mrksich, M.; Whitesides, G. M. *Anal. Chem.* 1997, 69, 3321-3328. Ramsden, J. J. *Chem. Soc. Rev.* 1995, 24, 73-78. Fainerman, V. B.; Lucassen-Reynders, E.; Miller, R. *Colloids Surf. A* 1998, 143, 141). This has spurred the development of alternative approaches to preserve the native conformation of proteins including 3-dimensional matrixes like hydrogels, and polyacrylamide (Arenkov, P.; Kukhtin, A.; Gemmel, A.; Voloshchuk, S.; Chupeeva, V.; Mirzabekov, A. *Anal. Biochem.* 2000, 278, 123-131. Kiyonaka, S.; Sada, K.; Yoshimura, I.; Shinkai, S.; Kato, N.; Hamachi, I. *Nature Materials* 2004, 3, 58-64.), cutinase-directed antibody immobilization onto SAMs (Kwon, Y.; Han, Z.; Karatan, E.; Mrksich, M.; Kay, B. K. *Anal. Chem.* 2004, 76, 5713-5720), and the coupling of biotinylated antibodies onto streptavidin coated surfaces (Peluso, P.; Wilson, D.; Do, D.; Tran, H.; Venkatasubbaiah, M.; Quincy, D.; Heidecker, B.; Poindexter, K.; Tolani, N.; Phelan, M.; Witte, K.; Jung, L.; Wagner, P.; Nock, S. *Anal. Biochem.* 2003, 312, 113-124). In addition, the arrays need to remain hydrated throughout the entire manufacturing process in order to prevent protein denaturation (Macbeath, G.; Schreiber, S. L. *Science* 2000, 289, 1760-1763). DNA microarrays, on the other hand, are typically electrostatically absorbed (via spotting) unto amine surfaces.

One option for detecting both DNA and proteins on the same slide would be to pattern both functional groups used to immobilize DNA and protein onto the same substrate, although this would significantly increase the complexity and engineering of the system. Alternatively, a compatible surface may be an activated ester glass slide to which amine-DNA and proteins can both covalently attach. However, the inventors have found that the loading capacity of these slides for DNA is diminished, resulting in poor signal intensity when compared with DNA printed on conventionally prepared amine slides. In addition, unreacted esters are hydrolyzed back to carboxylic acids, which are negatively charged at normal hybridization buffers (pH 7), electrostatically reducing the DNA interaction. Moreover, to interrogate cells and proteins, the best surface to reduce non specific binding of cells while maintaining full antibody functionality is acrylamide (Soen, Y.; Chen, D. S.; Kraft, D. L.; Davis, M. M.; Brown, P. O. *PLoS Biology* 2003, 1, (3), 429-438. Boozer, C.; Ladd, J.; Chen, S.; Yu, Q.; Homola, J.; Jiang, S. *Anal. Chem.* 2004, 76, 6967-6972), which is incompatible with DNA.

Additionally, by using DNA as a common assembly strategy for cells, cDNAs, and proteins, the substrate conditions for high DNA loading onto the spotted substrates, and for complementary DNA loading on the antibodies can be optimized. This leads to highly sensitive sandwich assays for protein detection, as well as high efficiency cell sorting (compared with traditional panning).

Example 11

Fabrication of Microfluidic Devices

Microfluidic-based assays offer advantages such as reduced sample and reagent volumes, and shortened assay times (Breslauer, D. N.; Lee, P. J.; Lee, L. P. *Mol. BioSyst.* 2006, 2, 97-112). For example, under certain operational conditions, the surface binding assay kinetics are primarily determined by the analyte (protein) concentration and the analyte/antigen binding affinity, rather than by diffusion (Zimmermann, M.; Delamarche, E.; Wolf, M.; Hunziker, P. *Biomedical Microdevices* 2005, 7, (2), 99-110). A microfluidics-based polynucleotide-encoded-protein approach was evaluated by bonding a polydimethylsiloxane (PDMS)-based microfluidic channel on top of a DNA microarray.

In particular, microfluidic channels were fabricated from polydimethylsiloxane (PDMS) using conventional soft lithographic techniques. The goal was to fabricate robust microfluidics channels that could be disassembled after the surface assays were complete for optical analysis. Master molds were made photolithographically from a high resolution transparency mask (CadArt) so that the resulting fluidic network consisted of 20 parallel channels each having a cross-sectional profile of 10×600 μm and were 2 cm long. This corresponds to channel volumes of 120 nl. A silicone elastomer (Dow Corning Sylgard 184™) was mixed and poured on top of the mold. After curing, the PDMS was removed from the mold and sample inlet and outlet ports punched with a 20 gauge steel pin (Technical Innovations™). The microfluidic channels were then aligned on top of the microarray and bonded to the substrate in an 80° C. oven overnight.

Example 12

Microfluidics-Based Assay Procedures Using DNA Encoded Antibodies

Microfluidic devices were interfaced with 23 gauge steel pins and Tygon™ tubing to allow pneumatically controlled flow rates of ~0.5 μl/min. Several assays were performed in Tris Buffered Saline (TBS), which was found to be better than 1×SSC and PBS in terms of reduced background noise. Each channel was blocked with 1.0% BSA in TBS prior to exposure to DNA-antibody conjugates or immunoassay pairs for 10 minutes under flowing conditions. After a 10 minute exposure to conjugates or antigens under flowing conditions, channels were washed with buffer for 2 minutes and the microfluidics disassembled from the glass slide in order to be scanned. Immediately prior to imaging, the entire slide was briefly rinsed in TBS, blown dry and imaged on an array scanner as described above.

In a first series of assays, two goat α-human IgG (labeled with Alexa594 or Alexa 647) were tagged with oligos A1' and B1' respectively and introduced into a microfluidic device bonded on top of a DNA microarray with corresponding complementary strands A1 and B1 along with non-complementary strand C1. No polynucleotide-encoded conjugate encoded to spot C1 was added. After flowing at ~0.5 μl/min for 10 minutes, the microfluidic PDMS slab was removed and the glass slide imaged. The results illustrated in FIG. 14 show that the antibody conjugates self-assembled at precise spatial locations encoded by the pendant oligonucleotide in <10 minutes (see FIG. 14), consistent with the time scales reported on DNA hybridization in microfluidics (Erickson, D.; Li, D.; Krull, U. *Anal. Biochem.* 2003, 317, 186-200. Bunimovich, Y.; Shin, Y.; Yeo, W.; Amori, M.; Kwong, G.; Heath, J. *J. Am. Chem. Soc.* 2006 (web release Dec. 1, 2006) DOI: 10.1021/ja065923u. Wei, C.; Cheng, J.; Huang, C.; Yen, M.; Young, T. *Nucleic Acids Research* 2005, 33, (8), 1-11). To validate the polynucleotide-encoded protein strategy for protein detection, further assays were performed where encoded antibodies were utilized to detect cognate antigens in a variant of standard immunoassays.

In a standard immunoassay (Engvall, E.; Perlmann, P. O. *J. Immunol.* 1972, 109, 129-135), a primary antibody is adsorbed onto a solid support, followed by the sequential introduction and incubation of the antigen-containing sample and secondary labeled "read-out" antibody, with rinsing steps in between. In order to simplify this conventional five step immunoassay, the encoding power of the DNA encoded antibodies was used to position the entire sandwich complex to the appropriate location for multiplexed readout, reducing the assay to a single step.

In particular, a non-fluorescent, DNA-encoded 1° antibody was combined with antigen and a fluorescently-labeled (no DNA) 2° antibody. Under these conditions, a fluorescent signal will be spatially encoded only if an antibody-antigen-antibody sandwich is successfully formed in homogeneous solution and localized onto the microarray.

In particular in a first further series of assays, upon introduction of DNA-encoded antibodies against two cytokines, human IFN-γ and TNF-α, cognate antigens and fluorescently-labeled 2° antibodies. The DNA-encoded antibody sandwich assays self-assembled to their specific spatial locations where they were detected, as shown in FIG. 15*a*. This multi-protein immunoassay also took 10 minutes to complete.

The sensitivity limits of a microfluidics, DNA encoded antibody-based sandwich immunoassay, was investigated in a second series of assays using a third interleukin, IL-2. The results are shown in FIG. 15*b* and FIG. 15*c* wherein visualization was performed using a fluorescent 2° antibody (panel b) and Au electroless deposition as a visualization and amplification strategy (panel c), respectively.

Using a fluorescent readout strategy, the assay peaked with a sensitivity limit of around 1 nM on slides printed at saturating concentrations of 5 μM of complementary DNA (data not shown). For the human IL-2 concentration series, primary DNA-antibody conjugates were laid down first on the surface, before exposure to antigen and secondary antibody. This is because at lower concentrations of antigen, the signals decrease, due to the high ratio of antigen-unbound primary antibody competing with antigen-bound primary for hybridization to the DNA array. By first exposing the array to the primary DNA-antibody conjugate, excesses were washed away before subsequent exposure to antigen and secondary antibody, increasing signal.

Several strategies were employed to increase the sensitivity. First, the applicants reasoned that increasing the loading capacity of the glass slide for DNA will increase the density of polynucleotide-encoded conjugates localized and therefore, increase the number of capture events possible. Conventional DNA microarrays are printed on primary amine surfaces generated by reacting amine-silane with glass (Pirrung, M. *Angew. Chem. Int. Ed.* 2002, 41, 1276-1289). DNA strands are immobilized through electrostatic interactions between the negative charges on the phosphate backbone of DNA and the positive charges from the protonated amines at neutral pH conditions. To increase the loading capacity of the slide, poly-lysine surfaces were generated, increasing both the charge density as well as the surface area of interaction with DNA. By adopting these changes, it became possible to print complementary DNA at saturating concentrations of 100 μM on the glass slides. Correspondingly, the sensitivity of the fluorescent based assays increased to 10 pM (FIG. 15*b*).

In a different visualization approach, Au nanoparticle-labeled 2° antibodies were used, followed by electroless metal deposition (Hainfeld, J. F.; Powell, R. D., Silver- and Gold-Based Autometallography of Nanogold. In *Gold and Silver Staining Techniques in Molecular Morphology*, Hacker, G. W.; Gu, J., Eds. CRC Press: Washington, D.C., 2002; pp 29-46), to further amplify the signal and transform a florescence based read out to an optical one. This is possible since spatial, rather than colorimetric multiplexing, is utilized.

In particular, microfluidics-based Au amplification experiments were performed in a manner similar to the one disclosed above, with the notable exception that a biotin-secondary antibody was used instead of a fluorescently labeled antibody. Subsequently, Au-streptavidin (Nanoprobes) was introduced into each channel (3 ng/µl) for 10 minutes, after which the channels were thoroughly rinsed with buffer. After removal of the PDMS, the entire slide was then amplified with gold enhancer kit (Nanoprobes) according to manufacturer's protocol.

Adopting these improvements, the presence of IL-2 interleukin can be readily detected at a concentration limit less than 10 fM (FIG. 15c), representing at least a 1000-fold sensitivity increase over the fluorescence based microfluidics immunoassay. In comparison, this method is 100-1000 fold more sensitive than conventional ELISA (Crowther, J. R., ELISA; Theory and Practice. In *Methods in Molecular Biology*, Humana Press Inc.: Totowa, N.J., 1995), and 150 times more sensitive than the corresponding human IL-2 ELISA data from the manufacturer (http://www.bdbiosciences.com/ptProduct.jsp?prodId=6725).

The results of these experiments show an improved sensitivity of the assays performed through sequential exposition of the reagent when compared to 1 step immunoassay, especially at lower concentrations of antigen. This is most likely due to competitive binding between DNA antibody conjugates with and without cargo for hybridization unto the underlying DNA microarray. By sequentially exposing the array to polynucleotide-encoded conjugate, antigen, and then secondary antibody, the sensitivities were increased. The most appropriate approach has to be selected in view of the desired results in term of convenience and sensitivity. It should still be stressed however, that maximum signal is still reached under microfluidic flowing conditions within 10 minutes for each step. Thus in a fully automated device, a complete microfluidic immunoassay with sensitivities down to 10 fM can be obtained in 1 hour (including a 30 minute step for Au amplification).

Example 13

Target-Quantitation of Using DNA Encoded Antibody Labeled with Metal Nanoparticles Digital proteomics were detected using DNA encoded antibody in combination with DNA arrays according to the strategy described in FIGS. 16 and 17. In particular, assays have been performed to detect certain cytokines (IL2, TNF-α and IFN-γ). All experiments were performed in a manner analogous to the 3-step immunoassays described above with the notable exception that a 40 nm Au particle is used and the detection scheme is a dark field light scattering microscope.

In particular, in the digital approach the 2° antibodies were labeled with 40 nm Au nanoparticles, which are readily detected by dark-field light scattering microscopy. More specifically a 40 nanometer Au nanoparticle-Streptavidin conjugate was used as the detection probe for the digital assay.

Figure 18:
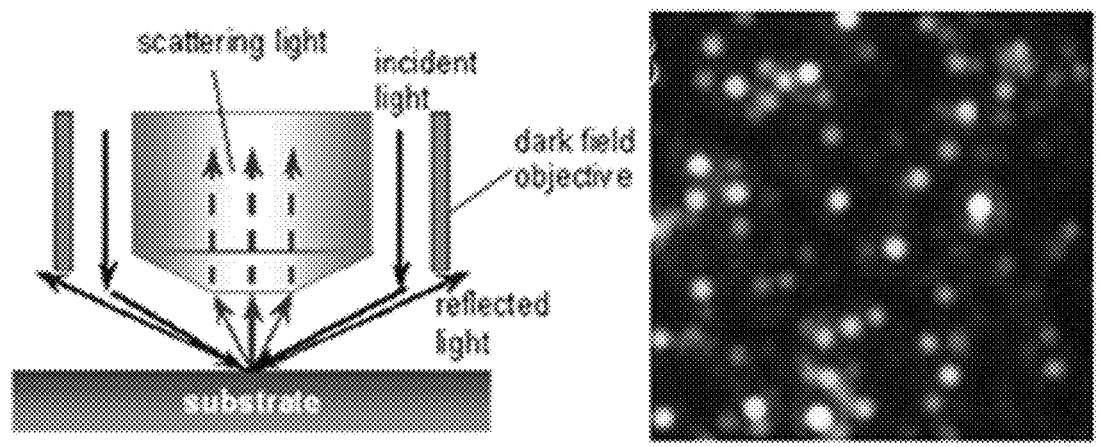
FIG. 18 is a schematic illustration of a device and related method to detect a signal from polynucleotide-encoded antibodies labeled with metal nanoparticules according to an embodiment of the methods and systems herein disclosed.

Detection of the relevant digital immunoassays was performed with the method illustrated in FIG. 18. According to the method illustrated in FIG. 18, scattered light is measured using a dark-field microscope objective. The plasmonic response of even very small Au particles is readily picked detected. The individual particles are counted either manually or using an automated software package for particle counting. Note that the scattering color of all of the particles is very similar—yellow-to-green. This is because the Au nanoparticles (10) are of a fairly narrow size range (~60 nanometers diameter). An optical filter can be utilized in the light scattering microscope to eliminate all other scattered colors and thus reduce background.

The results of the experiments are shown in FIGS. 19 to 22 wherein the conjugates are visualized using Rayleigh light scattering.

The sensitivity of the digital assay performed according to an embodiment of the methods and systems herein disclosed, is demonstrated in FIGS. 19 and 20 in which a concentration series of TNF-α is presented. The signal from this protein can be easily identified at concentrations as low as 100 attoMolar. FIGS. 19 and 20 show the representative dark field images of TNF-α Digital immunoassays performed at different concentrations with a method and system herein disclosed. ImageJ™, a scientific graph processing software provided by NIH, was used automatically count the particle numbers. The number of gold nanoparticles vs TNF-α concentration is plotted in the histogram of FIG. 20.

Figure 21:
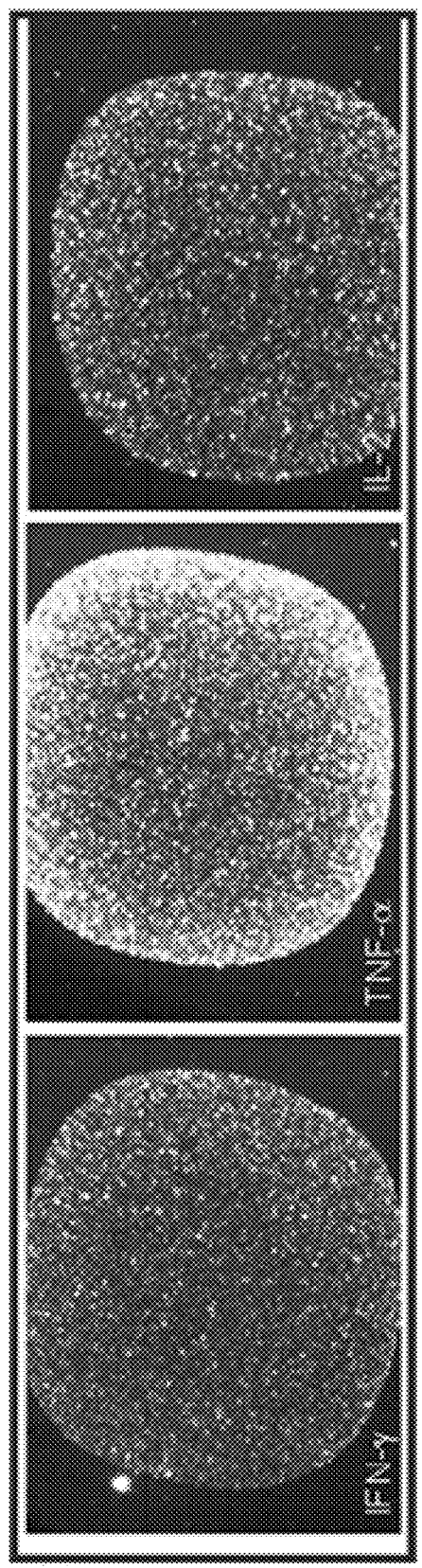
FIG. 21 shows detection of a proteomic of 3 proteins (IFN-γ, TNF-α and IL-2) from tissue culture media spiked with the three proteins with a method and system herein disclosed wherein the detection is performed using Au electroless deposition as a visualization and amplification strategy. Panel a shows detection of IFN-γ; Panel b shows detection of TNF-α; Panel c shows detection of IL-2.

To further assess the capability of this new technique in serum measurement, the above mentioned three cytokine proteins (IL2, TNF-α and IFN-γ) were spiked in human serum (purchased from Sigma-Aldrich) and the same AuNP based assay performed above, was conducted. The results are shown in FIG. 21. In particular, the images of Panel a were collected from a serum sample that was spiked with the three proteins: IFN-γ; TNF-α, and IL-2. The images of Panel b are from a digital immunoassay that was measured from the serum of a healthy human according to an embodiment of the methods and systems herein disclosed. All three of these proteins are typically present at below-detectable concentrations in human serum. TNF-α is below the detectable limit, but IFN-γ and IL-2 are present at the few femtoMolar ($10^{-15}$M) concentration levels. This amount of protein is well below the detection limit of a conventional absorbance or fluorescent ELISA or even immunoassay performed with another embodiment of the methods and systems herein disclosed.

It was found that the method according to the embodiments exemplified above worked well in serum, with high sensitivity and very little background noise. It is significant that the Digital immunoassay embodiment was sensitive to cytokines, which are biologically informative molecules but are present in trace quantities in pure, healthy human serum. As shown in FIG. 21 right, signals corresponding to human IFN-γ and IL-2 are present while TNF-α was not detected. This result illustrates the capabilities of methods and systems herein disclosed wherein detection is performed using metal nanoparticles.

Figure 22:
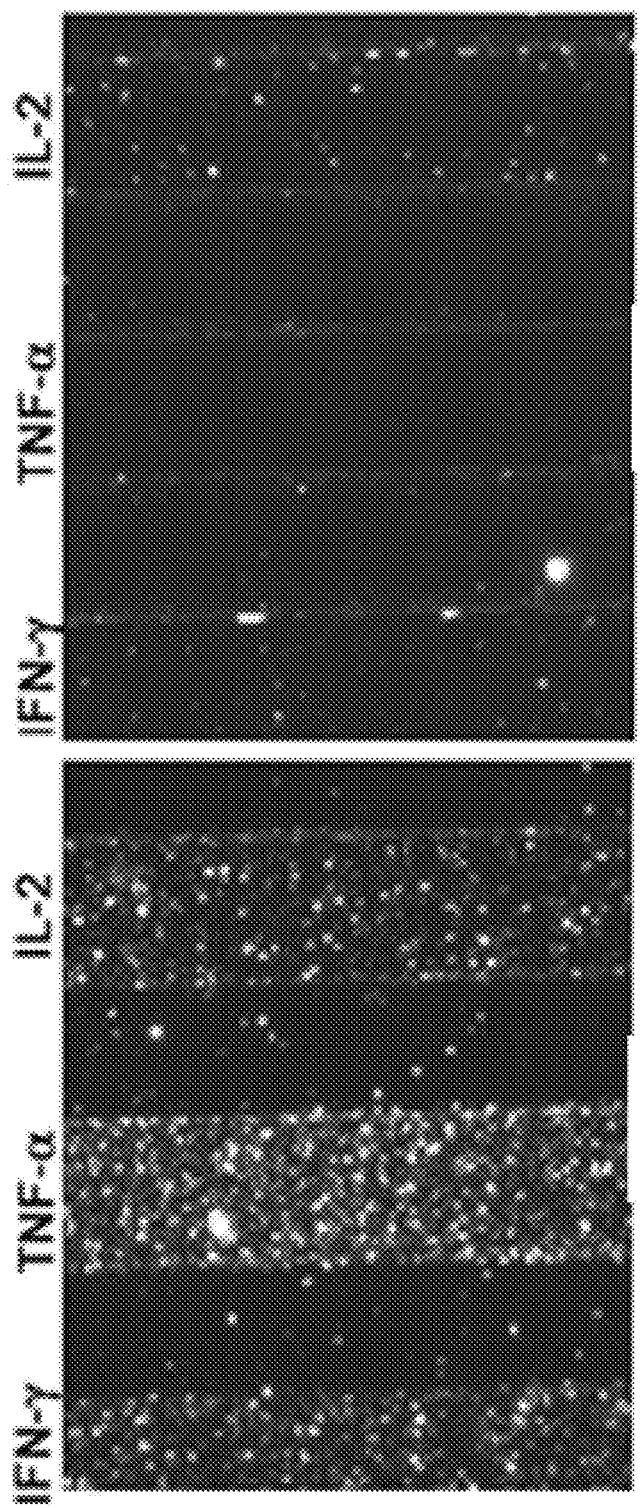
FIG. 22 shows detection of a proteomic of 3 proteins (IFN-γ, TNF-α and IL-2) from a serum sample spiked with the three proteins (Panel a) and from the serum of a healthy human (Panel b) with a method and system herein disclosed wherein the detection is performed using Au electroless deposition as a visualization and amplification strategy.

The detection of the above mentioned three human cytokine proteins, all prepared at identical concentrations was tested (FIG. 22). In particular, Three different ssDNA' molecules were spotted onto the substrate, with each ssDNA' being complementary to ssDNA oligomers that were labeled onto the 1° ABs: anti-IFN-; anti-TNF-, and anti-IL-2. 2oABs, labeled with 60 nanometer diameter Au nanoparticles, were introduced after the substrate had been exposed to the serum/protein mixture. The Au nanoparticles are visualized using a dark-field light scattering miscroscope.

The results shown in FIG. 22, can be unambiguously visualized and, in agreement with fluorescence-based assay, TNF-α exhibits the best signal intensity due to the high affinity of the 1° anti-TNF-α AB.

It should be noted that the background is near zero, and that the dynamic range of detected proteins is at least $10^6$. These types of assays have been utilized to detect certain cytokines (IL2, TNF-α and IFN-γ) out of healthy human serum. This has not been previously possible, as those proteins are present (by our measurements) at a level of only 1-5 femtoM. It is to be noted that once the antibody/protein affinities have been characterized, these types of assays are absolute and quantitative—meaning that they do not require calibration.

The digital detection of molecules with the methods and systems herein disclosed is readily adapted into microfluidics environments (the results from FIG. 21 were carried out in a microfluidic environment). In addition to the sample size and time-scale benefits that accompany this type of microfluidics immunoassay, there are other advantages. For example, since the entire assay is performed in solution prior to read-out, protein denaturation (a concern for spotted antibody microarrays) does not reduce binding efficiency. In addition, any assay that involves substrate-supported antibodies, would not have survived microfluidic chip assembly (which involved an extended bake at 80° C.). That procedure was designed to yield robust PDMS microfluidics channels that could then be disassembled for the optical readout step.

Another benefit of performing solution phase assays is that the orientational freedom enjoyed by both the antigens and antibodies ensures that the solid support will not limit the access of analytes to the binding pocket of the capture agent.

Example 14

Diagnostic Methods and System

Some initial calibration and quantitation of methods and systems herein disclosed for the analysis of biomarkers was performed in the PI3K pathway that is perturbed in many cancers, in particular glioblastoma. In particular, in FIG. 23, an embodiment is illustrated wherein the technology is applied to the detection of the biomarker pten, which is an important marker in glioblastoma (brain cancer).

Figure 23:
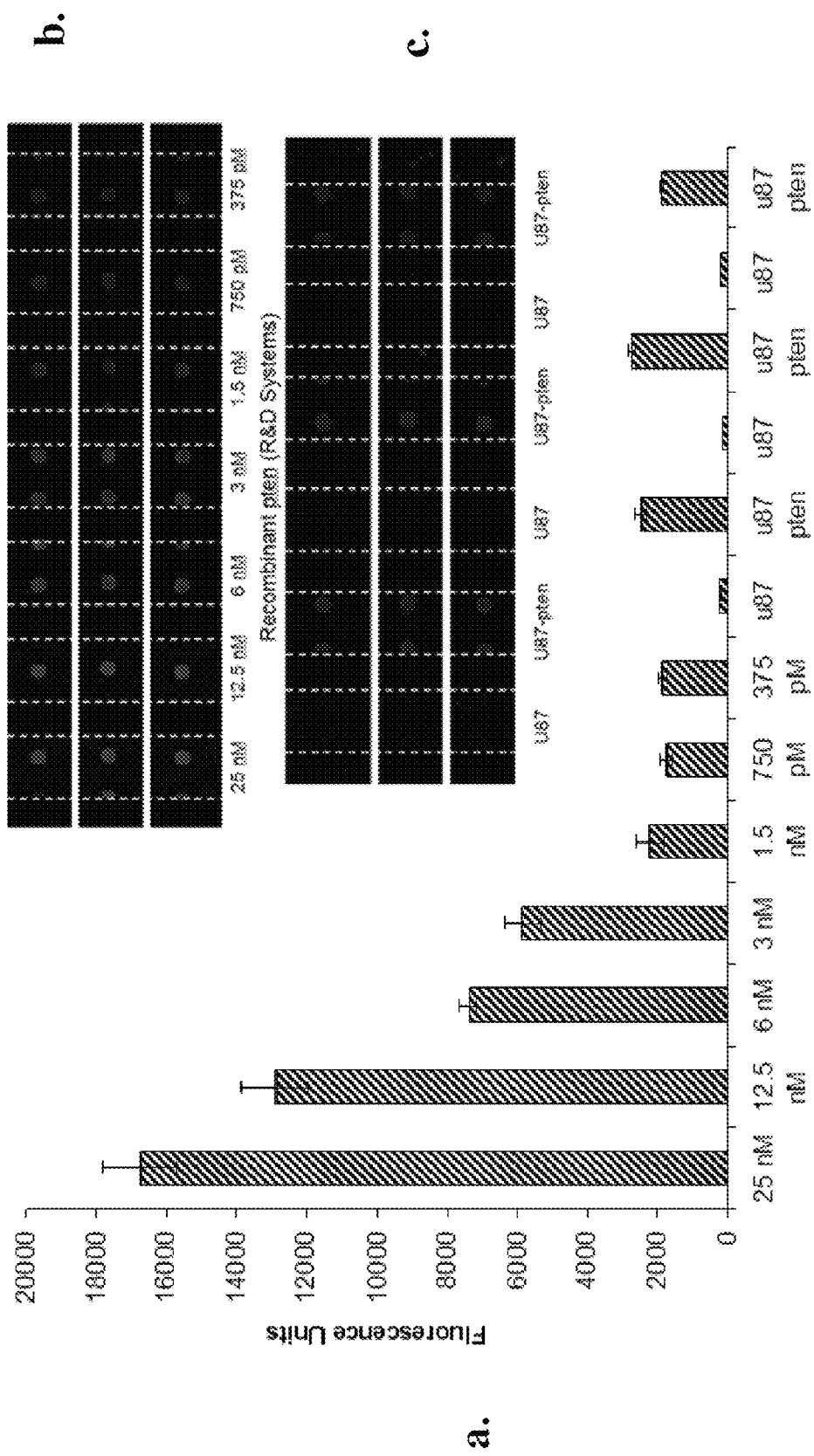
FIG. 23 is a diagram illustrating the calibration and quantification of the protein marker, Pten, with an embodiment of the methods and systems herein disclosed; Panel a shows a diagram wherein the average fluorescent intensity of the signal detected from the microfluidic experiments illustrated in Panels b and c, is illustrated; Panel b shows the raw data from the calibration lanes for recombinant pten; Panel c shows the raw fluorescent data from the samples from two cell lines, one is the null U87, expressing basal levels of pten, and the other is the U-87-pten overexpressing cell samples.

Methods and systems herein disclosed have been used in a fluorescent based assay first to calibrate a device by using recombinant pten as the standard (FIG. 23, Panels a and b). The calibration of the protein pten is shown with the left 7 bins, ranging from 25 nM to 375 pM. The right 3 bins represent pten-positive and pten-null samples. By comparing with the calibration bins, one can interpolate the concentration of pten to be around 1 nM. The inventors then proceeded to quantitate pten expression levels in the glioblastoma cell line U87 (Panels a and c). It is apparent that reasonable levels of pten (1 nM) are detectable using methods and systems herein disclosed as illustrated in FIG. 23.

With the methods and systems herein disclosed is also possible to perform detecting and relevant analysis of biomarkers in serum as an indication to the health state of an individual. Specifically, liver toxicity studies can be performed using the methods and systems herein disclosed. The results in liver are particularly interesting because the liver is the second largest organ in the human body (the first is the skin) and is in constant contact with the blood. Thus it is highly likely that perturbations at this organ will result in a notable change in the amount of protein biomakers found in serum that are liver specific.

An exemplary pathway from serum biomarker discovery to clinical validation is illustrated in FIG. 24.

A first step in serum biomarker discovery involves the proteomic analysis of the proteins in the blood via current state of the art in tandem mass spectrometry. Accordingly an initial protein list of about 25 proteins was discovered to be upregulated or downregulated following administration of high levels of acetomaniphen to murine model using tandem mass spectrometry (FIG. 24 Panel a (1). In particular, the peptides that are detected are mapped back to generate a list of candidate protein biomarkers. These biomarkers and their associated capture agents (antibodies) are screened and verified using the state of the art in surface plasmon resonance. In particular, a particularly effective antibody pairs was validated using SPR (FIG. 24 Panel b (2). Finally to enable highly sensitive, multiplexed, monitoring, these verified protein capture agents are translated into a microfluidic system according to an embodiment herein disclosed, allowing the monitoring of serum biomarkers in blood. In particular, a chip was designed and tested to detect 4 liver specific serum proteins and 3 immune specific proteins from whole serum (FIG. 24 Panel c (3). The results shown in FIG. 24 indicate that all targets were detected without difficulty from serum.

All of the above demonstrations have been carried out in either murine or human sera samples or both.

The examples set forth above are provided to give those of ordinary skill in the art a complete disclosure and description of how to make and use the embodiments of the devices, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Detailed Description, and Examples is hereby incorporated herein by reference. Further, the hard copy of the sequence listing submitted herewith and the corresponding computer readable form are both incorporated herein by reference in their entireties.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains. Although any methods and materials similar or equivalent to those described herein can be used in the practice for testing of the specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

What is claimed is:

1. A target detection method comprising:
combining polynucleotide-encoded proteins complementary to substrate polynucleotides with the substrate polynucleotides bound to a substrate and a sample containing targets to form hybridized polynucleotide-encoded protein target complexes, wherein the polynucleotide-encoded proteins comprise orthogonal polynucleotide-encoded proteins comprising polynucleotide sequences selected from the group consisting of SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18; and
detecting the hybridized polynucleotide-encoded protein target complexes.

2. A target detection method comprising:
combining polynucleotide-encoded proteins with a sample containing targets to form polynucleotide-encoded protein target complexes, wherein the polynucleotide-encoded proteins comprise a first and second group of polynucleotide-encoded proteins, wherein the first group specifically binds to a first target and the second group binds to a second target, and wherein the first and second group of polynucleotide-encoded proteins are orthogonal to one another and comprise polynucleotide sequences selected from the group consisting of SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18;

hybridizing the polynucleotide-encoded protein target complexes to complementary substrate bound substrate polynucleotides; and detecting the hybridized polynucleotide-encoded protein target complexes.

3. A target detection method comprising:

combining a) labeled polynucleotides complementary to both a target polynucleotide and a first group of substrate polynucleotides, b) polynucleotide-encoded antibodies complementary to a second group of substrate polynucleotides, c) the first and second group of substrate polynucleotides bound to a substrate, and d) a sample containing targets to form i) substrate polynucleotides hybridized to labeled polynucleotide-target polynucleotide complexes, and ii) substrate polynucleotides hybridized to polynucleotide-encoded antibody target complexes; and detecting the labeled polynucleotide-target polynucleotide complexes and the polynucleotide-encoded antibody target complexes.

4. The method of claim 3 further wherein the labeled polynucleotides are orthogonal to the polynucleotide-encoded antibodies.

5. The method of claim 4, wherein the orthogonal polynucleotide sequences are selected from the group consisting of SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

6. The method of claim 5, wherein the hybridization step further comprises a hybridization of 20 complementary bases.

* * * * *

UNITED STATES PATENT AND TRADEMARK OFFICE
CERTIFICATE OF CORRECTION

| | |
|---|---|
| PATENT NO. | : 8,354,231 B2 |
| APPLICATION NO. | : 12/652000 |
| DATED | : January 15, 2013 |
| INVENTOR(S) | : Kwong et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 229 days.

Signed and Sealed this
Seventh Day of May, 2013

Teresa Stanek Rea
*Acting Director of the United States Patent and Trademark Office*